United States Patent
Li et al.

(10) Patent No.: US 12,121,597 B2
(45) Date of Patent: Oct. 22, 2024

(54) HIGH-INTENSITY FOCUSED ULTRASOUND-INDUCED MECHANOCHEMICAL TRANSDUCTION IN SYNTHETIC ELASTOMERS

(71) Applicant: THE BOARD OF TRUSTEES OF THE UNIVERSITY OF ILLINOIS, Urbana, IL (US)

(72) Inventors: King C Li, Urbana, IL (US); Jeffrey S Moore, Savoy, IL (US)

(73) Assignee: The Board of Trustees of the University of Illinois, Urbana, IL (US)

(*) Notice: Subject to any disclaimer, the term of this patent is extended or adjusted under 35 U.S.C. 154(b) by 770 days.

(21) Appl. No.: 16/654,569

(22) Filed: Oct. 16, 2019

(65) Prior Publication Data

US 2020/0121810 A1 Apr. 23, 2020

Related U.S. Application Data

(60) Provisional application No. 62/817,113, filed on Mar. 12, 2019, provisional application No. 62/748,092, filed on Oct. 19, 2018.

(51) Int. Cl.
*A61K 49/00* (2006.01)
*A61K 41/00* (2020.01)
*G01N 21/70* (2006.01)

(52) U.S. Cl.
CPC ...... *A61K 49/0054* (2013.01); *A61K 41/0028* (2013.01); *G01N 21/70* (2013.01)

(58) Field of Classification Search
CPC . G01N 21/70; A61K 49/0054; A61K 41/0028
See application file for complete search history.

(56) References Cited

U.S. PATENT DOCUMENTS

| | | | |
|---|---|---|---|
| 8,236,914 B2 | 8/2012 | Potisek et al. | |
| 8,398,692 B2 | 3/2013 | Zhang et al. | |
| 8,603,790 B2 | 12/2013 | Zhang et al. | |
| 9,079,940 B2 | 7/2015 | Deisseroth et al. | |
| 9,278,159 B2 | 3/2016 | Boyden et al. | |
| 2008/0044472 A1* | 2/2008 | Garcia | A61P 29/00 424/93.1 |
| 2009/0028946 A1* | 1/2009 | Sheardown | A61K 41/0028 424/487 |
| 2011/0125080 A1 | 5/2011 | Shi et al. | |
| 2012/0277573 A1 | 11/2012 | Chang et al. | |
| 2013/0171116 A1* | 7/2013 | Shoham | A61L 27/383 435/325 |
| 2016/0041177 A1* | 2/2016 | Brayman | A61K 49/0095 424/9.6 |
| 2017/0225395 A1* | 8/2017 | Boydston | B33Y 80/00 |
| 2018/0357927 A1* | 12/2018 | Parker | G09B 23/28 |

FOREIGN PATENT DOCUMENTS

| | | | | |
|---|---|---|---|---|
| CN | 103570872 A | * | 2/2014 | ............... C08F 2/48 |
| EP | 2305216 A1 | | 4/2011 | |
| WO | 2016118516 A1 | | 7/2016 | |
| WO | 2017062875 A1 | | 4/2017 | |

OTHER PUBLICATIONS

Wang et al., Polymers, 2018, 10, 994. (Year: 2018).*
Clough et al., Adv. Functional Materials, 2016,26, p. 9063-9074. (Year: 2016).*
Truong et al., ACS Macro Lett., 2017, 6, p. 657-662. (Year: 2017).*
Labusca et al., WJSC, May 26, 2018, 10(5), p. 43-56. (Year: 2018).*
Li et al, "Polymer Mechanochemistry: From Destructive to Productive", Accounts of Chemical Research, vol. 48, No. 8, pp. 2181-2190, (2015).
Kato et al, "Freezing-Induced Mechanoluminescence of Polymer Gels", ACS Macro Lett., vol. 7, No. 9, pp. 1087-1091, (2018).
Filonenko et al, "Dynamic Phosphorescent Probe for Facile and Reversible Stress Sensing", Advanced Materials, vol. 12, No. 22, Jun. 13, 2017.
Zhuk et al, "Toward an Understanding of Diamond sp2-Defects with Unsaturated Diamondoid Oligomer Models", J. Am. Chem. Soc., vol. 135, No. 20, pp. 6577-6586, Apr. 27, 2015.
Yizhar et al, "Optogenetics in Neural Systems", Neuron, vol. 71, No. 11, pp. 9-34, Jul. 14, 2011.
Zhang et al, "The Microbial Opsin Family of Optogenetic Tools", Cell, vol. 147, No. 23, pp. 1446-1457, Dec. 23, 2011.
Caruso et al, "Mechanically-induced chemical changes in polymeric materials", Chem Rev, vol. 109, No. 11, pp. 5755-5798, (2009).
Robb et al, "Regioisomer-specific mechanochromism of napthopyran in polymeric materials", J. Am. Chem. Soc., vol. 138, No. 38, pp. 12328-12331, Sep. 12, 2016.
Xia et al, "Ultrasound-Mediated Polymeric Micelle Drug Delivery", Therapeutic Ultrasound, pp. 365-384, (2016).
Chen et al, "Mechanically induced chemiluminescence from polymers incorporating a 1,2-dioxetane unit in the main chain.", Nature Chemistry, vol. 4, pp. 559-562, (2012).

* cited by examiner

*Primary Examiner* — Michael G. Hartley
*Assistant Examiner* — Leah H Schlientz
(74) *Attorney, Agent, or Firm* — Lathrop GPM LLP; Lisa Hillman

(57) ABSTRACT

Provided herein are compositions and methods for remotely and non-invasively subjecting targeted biological structures with light emissions or chromogenic changes.

17 Claims, 12 Drawing Sheets
(12 of 12 Drawing Sheet(s) Filed in Color)

A

B

Chromogenic PDMS (orange color)

C

D

Mechanoluminescent PDMS (blue light)

HIGH-INTENSITY FOCUSED ULTRASOUND-INDUCED MECHANOCHEMICAL TRANSDUCTION IN SYNTHETIC ELASTOMERS

PRIORITY

This application claims the benefit of U.S. 62/748,092, filed on Oct. 19, 2018, and U.S. 62/817,113 filed on Mar. 12, 2019, both of which are incorporated by reference in their entireties.

STATEMENT REGARDING FEDERALLY SPONSORED RESEARCH OR DEVELOPMENT

This invention was made with government support under contract number 5R01CA184091, awarded by the National Institutes of Health. The government has certain rights in the invention.

BACKGROUND

Generating light in vivo for applications such as optogenetic research is generally achieved by the implantation of optical fibers or devices. Methods are needed in the art to generate localized photon fluxes in vitro and in vivo without the use of optical fibers or devices.

DESCRIPTION OF THE DRAWINGS

The patent or application file contains at least one drawing executed in color. Copies of this patent or patent application publication with color drawing(s) will be provided by the Office upon request and payment of the necessary fee.

SUMMARY

Figure 1:
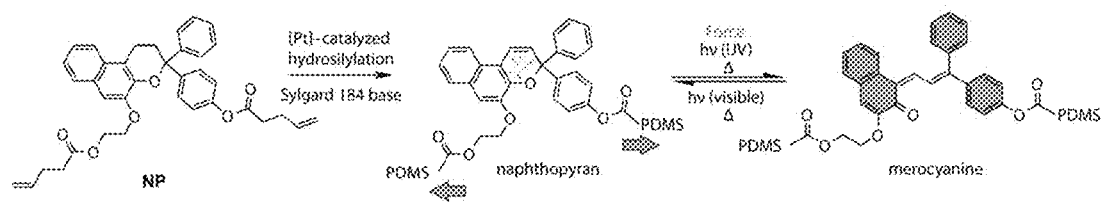
FIG. 1 shows synthesis of mechanochromic and mechanoluminescent PDMS materials: (A) 1.5 wt % NP (bisvinyl-terminated naphthopyran) is crosslinked into the PDMS network and isomerizes in response to mechanical force to generate an orange colored merocyanine species; (B) 1.5 wt % monofunctional NP-control is covalently appended to PDMS and insensitive to mechanical force. Both NP and NP-control isomerize to the colored merocyanine form under UV-light and high temperature; (C) 1.5 wt % dioxetane is crosslinked into the PDMS network and undergoes a cycloelimination reaction in response to mechanical force to generate blue light in the presence of 0.5 wt % of the sensitizer 9,10-diphenylanthracene (DPA); and (D) Physically incorporating 1.5 wt % dioxetane control with 0.5 wt % DPA gives an elastomeric control material that is insensitive to mechanical force.
Figure 1:
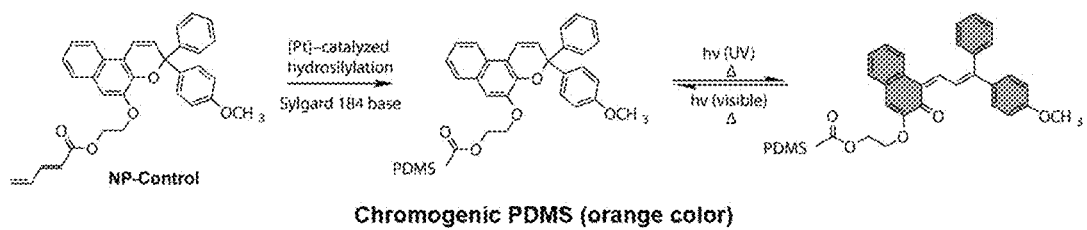
Figure 1:
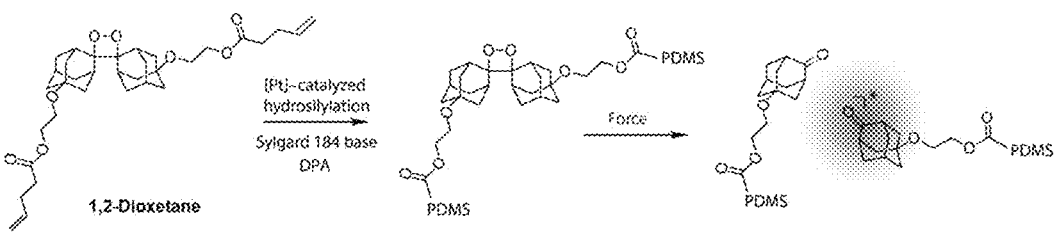
Figure 1:
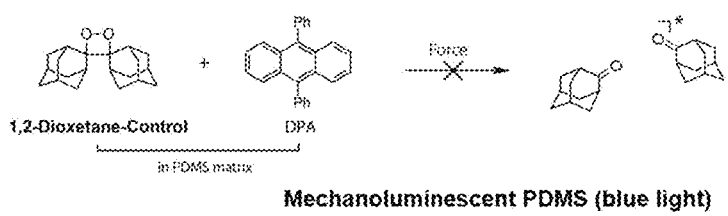

An embodiment provides a composition comprising a chromogenic or luminescent mechanophore covalently linked or non-covalently bonded to a gel or elastomer matrix, wherein the chromogenic or luminescent mechanophore is present in the gel or elastomer matrix at about 1.0 wt % to about 5 wt %. The gel or elastomer matrix can comprise polydimethylsiloxane (PDMS) or polyethylene glycol (PEG). The chromogenic or luminescent mechanophore can be, for example, naphthopyran, dioxetane, spiropyran, maleimide anthracene, or tetraarylsuccinonitrile tetraol. The composition can further comprises an energy acceptor such as perylene, anthracene, or psoralen. An energy acceptor can be present in the gel or elastomer matrix at about 0.1 wt % to about 10 wt %. The gel or elastomer matrix can further comprise one or more types of genetically modified cells. The one or more types of genetically modified cells can express one or more recombinant light sensitive proteins.

Another embodiment provides a composition comprising a luminescent or chromogenic mechanophore covalently linked or non-covalently bonded to a gel or elastomer matrix, wherein the luminescent or chromogenic mechanophore is present in the gel or elastomer matrix at about 1.0 wt % to about 5 wt %, and cells, cell culture, or tissue, wherein the gel or elastomer matrix is in contact with the cells, cell culture, or tissue. The gel or elastomer matrix can be present within the cells.

Still another embodiment provides a method of triggering a change in a biological activity of a cell or tissue. The method comprises contacting a gel or elastomer composition described herein with the cell or tissue or bringing the gel or elastomer composition into the vicinity of the cell or tissue, and subjecting the composition to high intensity focused ultrasound such that a light emission or chromogenic change is produced from the mechanophore. The light emission or chromogenic change triggers a change in the biological activity of the cell or tissue. The ultrasound can have a frequency of about 400 kHz to about 1 MHz. The focal size of the ultrasound can be about half the wavelength of the ultrasound to about 20 cm. Half the wavelength of the ultrasound when the ultrasound is from about 400 kHz to about 1 MHz is about 0.78 mm to about 2 mm (e.g. about 0.78, 0.9, 1.0, 1.25, 1.5, 1.75, 2.0 mm). The light emission can be blue (about 400-450 nm) or yellow (about 560-590 nm). The excitation pressure of the high intensity focused ultrasound can be about 2.1 MPa to about 3.3 MPa. The duration of the high intensity focused ultrasound can be about 5 seconds to about 120 seconds. The beam width of the transducer can be about 1 mm to about 30 cm. The beam intensity can be about 39.4 to about 376 $W \cdot cm^{-2}$.

Yet another embodiment provides a method for remotely and non-invasively activating a mechanophore in the vicinity of a cell, cell culture, tissue or patient. The method comprises implanting a gel or elastomer composition described herein within cell, cell culture, tissue, or patient; contacting the gel or elastomer composition with a cell, cell culture, tissue, or patient; or bringing the gel or elastomer composition into the vicinity a cell, cell culture, tissue, or patient. High intensity focused ultrasound is then directed to the composition such that the mechanophore is activated. In an embodiment no thermal increases are caused by the high intensity focused ultrasound. The activation can be a light emission or a chromogenic change. The cell, cell culture, tissue, or patient can comprise one or more genetically modified cells, wherein the genetically modified cells express one or more recombinant light sensitive proteins. The gel or elastomer matrix can comprise one or more genetically modified cells, wherein the genetically modified cells express one or more recombinant light sensitive proteins. Both the cell, cell culture, tissue, or patient and the gel or elastomer matrix can comprise genetically modified cells that express one or more genetically modified cells.

Another embodiment provides a method for illuminating a targeted structure of a cell, tissue, or patient comprising a light sensitive protein. The method comprises contacting or bringing into the vicinity of the cell, tissue, or patient a composition comprising a luminescent mechanophore covalently linked or non-covalently bonded to a gel or elastomer matrix, wherein the chromogenic or luminescent mechanophore is present in the gel or elastomer matrix at about 1.0 wt % to about 5 wt %. High intensity focused ultrasound is directed to the composition such that the mechanophore is activated and illuminates a targeted structure of a cell, tissue, or patient. The cell, cell culture, tissue, or patient can comprise one or more genetically modified cells, wherein the genetically modified cells express one or more recombinant light sensitive proteins. The gel or elastomer matrix can comprise one or more genetically modified cells, wherein the genetically modified cells express one or more recombinant light sensitive proteins. Both the cell, cell culture, tissue or patient and the gel or elastomer can comprise genetically modified cells that express one or more genetically modified cells.

The concept of sono-optogenetics is introduced herein. Sono-optogenetics couples high-intensity focused ultrasound (HIFU) with a mechanoluminescent gel or elastomer to generate a localized photon flux.

One challenge in exploiting polymer mechanochemistry in biological and clinical regimes is the lack of a compatible triggering system that enables noninvasive, spatiotemporal control of mechanochemical transformations. Provided herein are novel approaches that use high-intensity focused ultrasound (HIFU) to control the spatial location and period of mechanophore activation without causing irreversible damage to the sample. In an embodiment a HIFU-based triggering system can activate two different mechanochemical responses: a reversible color change and the emission of light. The HIFU systems can be used as a stimulus that provides on-demand, spatiotemporally resolved mechanical energy, and makes polymer mechanochemical transduction a potential means for minimizing invasive biomedical methods.

HIFU can trigger polymer mechanochemistry in an elastomeric network through mechanical deformation. A visible color change associated with mechanoactivation provides a simple read-out for initial investigations of HIFU-triggered polymer mechanochemistry. By irradiating crosslinked elastomer samples with HIFU, short sonication durations at moderate power and output pressures can provide suitable conditions to achieve mechanically-induced mechanophore activation within bulk materials. These HIFU conditions can successfully activate a mechanoluminescent mechanophore to emit colored light.

DETAILED DESCRIPTION

The compositions and methods are more particularly described below and the Examples set forth herein are intended as illustrative only, as numerous modifications and variations therein will be apparent to those skilled in the art. As used in the description herein and throughout the claims that follow, the meaning of "a", "an", and "the" includes plural reference unless the context clearly dictates otherwise. The term "about" in association with a numerical value means that the value varies up or down by 5%. For example, for a value of about 100, means 95 to 105 (or any value between 95 and 105).

Provided herein are triggering methods for mechanophores that perform various chemical reactions in response to mechanical stimuli, which are compatible with biological systems. Applications such as using mechanoluminescence to generate localized photon flux in vivo for optogenetics are provided. Methods of triggering mechanophores by using high-intensity focused ultrasound (HIFU) as a remote energy source are provided to drive spatially and temporally resolved mechanical-to-chemical transduction of mechanoresponsive polymers. HIFU setups capable of controlling the excitation pressure, spatial location, and duration of exposure are employed to activate mechanochemical reactions in a crosslinked elastomeric polymer in a noninvasive fashion. One embodiment provides the chromogenic isomerization of a naphthopyran mechanophore embedded in a polydimethylsiloxane (PDMS) network. Under HIFU irradiation evidence of the mechanochemical transduction is the reversible observation of a color change as expected for the isomerization. An elastomer or gel exhibits this distinguishable color change at the focal spot, depending on ultrasonic exposure conditions. Another embodiment provides HIFU irradiation that can successfully trigger a luminescent dioxetane, resulting in localized generation of visible blue light at the focal spot. In contrast to conventional stimuli such as UV light, heat, and uniaxial compression/tension testing, HIFU irradiation provides spatiotemporal control of the mechanochemical activation through targeted but noninvasive ultrasonic energy deposition. Targeted, remote light generation is useful in biomedical applications such as optogenetics where a light source is used to trigger a cellular response.

Luminescent and Chromogenic Mechanophores

A mechanophore is a mechanically-sensitive compound that responds to mechanical force with a chemical change. Chromogenic mechanophores such as naphthopyran are activated by mechanical force to exhibit a reversible color change, while luminescent mechanophores such as dioxetane are activated to emit chemiliuminescence. See, e.g., Li et al., Polymer Mechanochemistry: From Destructive to Productive, Accounts of Chemical Research 2015 48 (8), 2181-2190, incorporated by reference in its entirety.

Naphthopyran, dioxetane, spiropyran, maleimide anthracene, tetraarylsuccinonitrile tetraol (TASN tetraol) (tetraarylsuccinonitrile moieties can generate pink radicals that emit yellow light. are examples of mechanophores. See, Kato et al., Freezing-Induced Mechanoluminescence of Polymer Gels, ACS Macro Lett., 2018, 7 (9), pp 1087-1091). Dynamic phosphorescent $CuN_4$ complexes incorporated into the main chain of polyurethanes have also shown enhanced photoluminescence when incorporated into a polyurethane matrix and subjected to mechanical force. See, Filonenko & Khusnutdinova, Dynamic Phosphorescent Probe for Facile and Reversible Stress Sensing, Advanced Materials, 29:1700563 (2017).

Any mechanophore, for example a chromogenic or luminescent mechanophore, can be used in the compositions and methods described herein.

Gel or Elastomer Matrices

Gels are substantially dilute cross-linked systems that exhibit no flow when in the steady-state. Gel matrices can be any type of suitable gel, such as silicone gels, hydrogels. Other gels include, for example, arabinogalactan gel, arabinoxylan gel, galactan gel, galactomannan gel, lichenan gel, xylan gel, cellulose derivatives such as hydroxymethylpropyl cellulose, combined with a gel forming agent such as arabinogalactan, arabinoxylan, galactan, galactomannan, licenan, xylan, hydroxymethyl cellulose, protein gels, gelatin gels, whey protein gel, soy protein gel, casein gel, gels comprised of arabinogalactan; arabinoxylan; galactan; galactomannan; lichenan; xylan; casein; hyaluronic acid; chitosan; gum Arabic; carboxyvinyl polymer; sodium polyacrylate; carboxymethyl cellulose; sodium carboxymethyl cellulose; pullulan; polyvinylpyrrolidone; karaya gum; pectin; xanthane gum; tragacanth; alginic acid; polyoxymethylene; polyimide; polyether; chitin; poly-glycolic acid; poly-lactic acid; co-polymer of poly-glycolic and poly-lactic acid; co-polymer of poly-lactic acid and polyethylene oxide; polyamide; polyanhydride; polycaprolactone; maleic anhydride copolymer; poly-hydroxybutyrate co-polymer; poly(1,3-bis(p-carbophenoxy)propane anhydride); polymer formed by co-polymerization with sebacic acid or with poly-terephthalic acid; poly(glycolide-co-trimethylene carbonate); polyethylene glycol; polydioxanone; polypropylene fumarate; poly(ethyl glutamate-co-glutamic acid); poly(tert-butyloxy carbonylmethyl glutamate); poly-caprolactone; poly(caprolactone-co-butylacrylate); poly-hydroxybutyrate and copolymers thereof; poly(phosphazene); poly(D,L-lactide-co-caprolactone); poly(glycolide-co-caprolactone); poly(phosphate ester); poly(amino acid); poly(hydroxybutyrate); polydepsidpeptide; maleic anhydride copolymer; polyphosphazene; polyiminocarbonate; poly[(7.5% dimethyl-trimethylene carbonate)-co-(2.5% trimethlyene carbonate)]; polyethylene oxide; hydroxypropylmethylcellulose, poly(ethylene-co-vinyl acetate); isobutylene-based copolymer of isobutylene and at least one other repeating unit such as butyl acrylate: butyl methacrylate; substituted styrene such as amino styrene, hydroxy styrene, carboxy styrene, sulfonated styrene; homopolymer of polyvinyl alcohol; co-polymer of polyvinyl alcohol and at least one other repeating unit such as a vinyl cyclohexyl ether; hydroxymethyl methacrylate; hydroxyl- or amino-terminated polyethylene glycol; acrylate-based copolymer such as methacrylic acid, methacrylamide, hydroxymethyl methacrylate; ethylene vinyl alcohol copolymer; silicone based copolymer of aryl or alkyl siloxane and at least one repeating unit; polyurethane; heparan sulfate; RGD peptide; polyethylene oxide; chrondroitin sulfate; YIGSR peptides; keratan sulfate; VEGF biomimetic peptide; perlecan (heparan sulfate proteoglycan 2); modified heparin; fibrin fragments; and combinations thereof. Any suitable gel matrices can be used.

Hydrogels, gels, and elastomers can be made up of natural materials or synthetic materials or combinations thereof. Suitable gel or hyderogel matrices can be made up of, for example, collagen, fibrin, chitosan, hyaluronic acid, chondroitin sulfate, alginate, agar/agarose polyethylene (PE), polyethylene glycol (PEG), polyethylene oxide (PEO), polyethylene glycol diacrylate (PEGDA), poly(ethylene glycol)-dimethacrylate (PEGDMA) poly(oligoethylene glycol methacrylate, polyacrylamide, polylysine, oligo(poly(ethylene glycol) fumarate) (OPF), polydimethylsiloxane (PDMS), polypropylene (PP), poly(propylene fumarate) (PPF), poly(N-isopropylacrylamide) (PNIPA, PNIPAAm, NIPA, PNIPAA or PNIPAm), poly(lactic) acid (PLA), poly-L-lactide (PLLA), polyvinyl acetate (PVA), polysulfone, polyvinylchloride (PVC), polytetrafluoroethylene (PTFE), polyetheretherketone (PEEK), poly(lactic-co-glycolic acid) (PLGA), poly(propylene fumarate) (PPF), poly(aldehyde guluronate), Polycaprolactone (PCL), polyphenylene oxide (PPO), PEO-PPO-PEO, PLGA-PEG, PLGA, PEG-PLLA-PEG, PCL-PEG-PCL, PCLA-PEG-PCLA, PEG-PCL-PEG, acrylated forms of polyethylene glycol, acrylated forms of polydimethylsiloxane, acrylated forms of polyacrylamide, or combinations thereof.

Elastomer matrices are made up of polymers with viscoelasticity (i.e., both viscosity and elasticity). Any elastomeric materials can be used to make an elastomer matrix including, for example, thermoplastic elastomers, polyolefin elastermers, polydiene elastomers, poly(vinyl chloride), PDMS, PEG, natural rubber, heparinized polymers, hydrogels, polypeptide elastomers, and combinations thereof. Any suitable elastomer can be used.

In an embodiment a gel or elastomer matrix is biocompatible.

Hydrogels can be used, which are three-dimensional networks of hydrophilic polymer chains, in which retained water constitutes at least about 20% of the weight (for example about 20, 30, 40, 50, 60% or more). In an embodiment the retained water can be about 70, 60, 50, 40, 30, 25, 21% or less of the weight. In an embodiment a hydrogel matrix is biocompatible. A biocompatible hydrogel matrix performs its desired function, without eliciting significant undesirable local or systemic effects in the patient or recipient (e.g., cells, tissues, mammals), while generating the most appropriate beneficial cellular or tissue response.

In an embodiment, a gel or elastomer matrix is a PEG matrix that is not thiol-ene based. See, e.g., Bakaic et al., RSC Advances, 5:35469 (2015).

In an embodiment, one or more mechanophores are covalently crosslinked or non-covalently bonded to a gel or elastomer matrix providing a composition comprising, for example, a chromogenic or luminescent mechanophore covalently linked (by any suitable means) to a gel or elastomer matrix. A chromogenic or luminescent mechanophore can be present in the gel or elastomer matrix at about 0.5, 1.0, 2.0, 3.0, 4.0, 5.0, 6.0, 7.0 wt % or more. A chromogenic or luminescent mechanophore can be present in the gel or elastomer matrix at about 7.0, 6.0, 5.0, 4.0, 3.0, 2.0, 1.0, 0.5 wt % or less.

A gel or elastomer matrix can be any size or shape. For example, a gel or elastomer matrix can be a cylinder, sphere, plane, sheet, slab, irregular, or cube shape. A hydrogel can be have any dimension. In an embodiment a gel or elastomer matrix is about 1 mm, 5 mm, 10 mm, 20 mm, 50 mm or more thick.

In an embodiment, a chromogenic or luminescent mechanophore is not present in a solution or liquid (as an end product), but is non-covalently bonded, covalently linked or bonded, or covalently crosslinked to a gel or elastomer matrix. Crosslinking is the process of forming covalent bonds or relatively short sequences of chemical bonds to join polymer chains together. Non-covalent bonds can be, for example, hydrogen bonds, Van der Waals interactions, hydrophobic bonds, and/or ionic bonds.

Energy Acceptors

An energy acceptor can be included in a gel or elastomer matrix at about 0.1, 1.0, 2.0, 3.0, 4.0, 5.0, 6.0, 7.0, 8.0, 9.0, 10.0 wt % or more. Energy acceptors include, for example perylene, psoralen, psoralen, pyrene cholesteryloleate, acridine, porphyrin, fluorescein, rhodamine, 16-diazorcortisone, ethidium, transition metal complexes of bleomycin, transition metal complexes of deglycobleomycin organoplatinum complexes, alloxazines, vitamin Ks, vitamin L, vitamin metabolites, vitamin precursors, naphthoquinones, naphthalenes, naphthols and derivatives thereof having planar molecular conformations, porphorinporphyrins, dyes and phenothiazine derivatives, coumarins, quinolones, quinones, anthroquinones, 8-MOP, AMT, 7,8-dimethyl-10-ribityl, isoalloxazine, 7,8,10-trimethylisoalloxazine, 7,8-dimethylalloxazine, isoalloxazine-adenine dinucleotide, alloxazine mononucleotide, aluminum (III) phthalocyanine tetrasulonate, hematophorphyrin, and phthadocyanine.

In an embodiment, an energy acceptor has a lower energy than that of the excited ketone that is formed when a mechanophore such as dioxetane is subjected to stress.

One or more energy acceptors can be covalently crosslinked to the gel or elastomer matrix or can be non-covalently bonded to the gel or elastomer matrix through any means.

Genetically Modified Cells

One or more genetically modified cells (i.e., recombinant cells) can be present in a gel or elastomer matrix. One or more genetically modified cells, alternatively or additionally, can be present in a target structure, for example, cells, cell culture, tissue, or a patient. Cells can be genetically modified to express light sensitive proteins. A light sensitive protein can be, for example, an opsin protein such as a depolarizing opsin, a hyperpolarizing opsin, a stimulatory opsin, an inhibitory opsin, a chimeric opsin, and a step-function opsin. A light sensitive protein can be, for example, eBR (an enhanced version of bacteriorhodopsin from *Halobacterium salinarum*), *Guillardia theta* rhodopsin-3 (GtR3), halorhodopsin (NpHR; Halo), eNpHR 1.0, eNpHR 2.0, eNpHR 3.0, SwiChR (Step-Waveform Inhibitory ChannelRhodopsin), SwiChR 2.0, SwiChR 3.0, Mac (light-driven proton pump of *L. maculans*), Mac 3.0, Arch (archaerhodopsin), ArchT, Arch 3.0, ArchT 3.0, iChR, C1V1-T (a chimeric opsin variant), C1V1-TT (a chimeric opsin variant), Chronos (a highly light-sensitive and fast opsin), Chrimson (a complimentary red-activated opsin), ChrimsonR, CatCh, VChR1-SFO, ChR2-SFO, ChR2-SSFO, ChEF, ChIEF, Jaws, ChIoC, Slow ChIoC, iC1C2, iC1C2 2.0, iC1C2 3.0, ChR2 and ChR2 mutants with several single-amino-acid substitutions: ChR2(H134R) ($ChR2_R$), ChR2 (E123A) ($ChETA_A^1$), ChR2(T159C) (TC), ChR2(E123T/T159C) ($ChETA_{TC}$), ChR2(L132C) (CatCh), channelrhodopsin-1 (ChR1), channelrhodopsin-2 (Ch R2), and red-activatable channelrhodopsin (ReaChR).

Examples of opsins are described in, for example, U.S. Pat. Nos. 9,278,159, 8,603,790, 8,398,692, and 9,079,940; Yizhar et al. 2011, Neuron 71:9-34; Zhang et al. 2011, Cell 147:1446-1457, all of which are incorporated by reference herein in their entirety.

Nucleic acids encoding light sensitive proteins can be delivered to cells in vitro using well known methods in the art such that the cells recombinantly express light sensitive proteins. The recombinant cells can then be placed or linked into a gel or elastomer matrix as described herein. The recombinant cells can also be placed into cell culture, tissue, or a patient. A gel or elastomer matrix as described herein can then contact the cell, cell culture, tissue or patient or can be brought into the vicinity of the cell, cell culture, tissue or patient.

Light sensitive proteins can be delivered to cells in vivo using, for example, viral mediated gene delivery, electroporation, optoporation, ultrasound, hydrodynamic delivery, or the introduction of naked DNA either by direct injection or complemented by additional facilitators such as cationic lipids or polymers.

Lenti- and adeno-associated ("AAV") viral vectors have been utilized successfully to introduce opsins into mouse, rat, and primate brain. Other vectors include but are not limited to equine infectious anemia virus pseudotyped with a retrograde transport protein (e.g., Rabies G protein), and herpes simplex virus ("HSV").

Lentivirus is easily produced using standard tissue culture and ultracentrifuge techniques, while AAV can be reliably produced and has a good safety profile. AAV serotypes 1 and 6 can infect motor neurons following intramuscular injection in primates. Additionally, AAV serotype 2 has been shown to be expressed and well tolerated in human patients. AAV8, AAV5, and AAV2 have all been demonstrated to reliably deliver opsin proteins in vivo.

A viral vector, such as AAV or lentivirus can comprise a light sensitive protein expression cassette, which can comprise a light sensitive protein (e.g., ChR2, NpHR, etc.) and a promoter that can drive expression of the particular light sensitive protein within a targeted set of cells. The promoter can be specific for a targeted tissue. For example a human synapsin promoter ("hSyn") or human Thy1 promoter ("hThy1") are specific for expression in neurons; calcium/calmodulin-dependent kinase II promoters ("CAMKII"), are specific for expression in excitatory neurons, a subset of the neuron population. Alternatively, a ubiquitous promoter can be used, such as the human cytomegalovirus ("CMV") promoter or the chicken beta-actin ("CBA") promoter, each of which is not cell-type specific. Nucleic acids encoding light sensitive proteins can be delivered to a target structure.

High-Intensity Focused Ultrasound

High-intensity focused ultrasound (HIFU) can be used as a stimulus for precision medicine due to its non-invasive nature and superior ability to penetrate biological tissue compared to other spatiotemporally-resolved stimuli such as light. By focusing an ultrasonic wave onto a target location, the high intensity of irradiation achieves mechanical deformation and cavitation in response to the acoustic pressure wave, as well as localized heating from energy dissipation.

HIFU (e.g., FUS Instruments, Canada) can be used to generate continuous wave ultrasound at a center frequency of about 400 kHz to about 1 MHz. In an embodiment, an HIFU transducer is used at a center frequency of about 400, 500, 600, 700, 800, 900, or 1,000 kHz for about 5, 10, 20, 30, 60, 90, 120 seconds or more. The HIFU transducer can be at a focal distance of about 2,000, 1,000, 900, 800, 700, 600, 500, 400, 300, 200, 100, 90, 80, 70, 60, 50, 40, 30 mm or less to the gel or elastomer matrix or target structure. The effective acoustic pressure level triggered by the HIFU can be about 2.1, 2.2, 2.3, 2.4, 2.5, 2.6, 2.7, 2.8, 2.9, 3.0, 3.1, 3.2, 3.3 MPa or more. The intensity (I) the HIFU can be about 35, 39.4, 40, 50, 75, 100, 150, 200, 250, 300, 325, 350, 370, 375, 376, 380, 390, 400 $W \cdot cm^{-2}$ or more. The focal size of the ultrasound can be about half the wavelength of the ultrasound to about 1, 2, 3, 5, 10, 15, 20 cm or more. The beam width of the transducer can be about 1 mm, 10 mm, 50 mm, 100 mm, 200 mm, 30 cm or more. In an embodiment, the beam width of the transducer is about 1.3 mm to about 3.1 mm.

In an embodiment, a barrier is present between the HIFU transducer and the gel or elastomer matrix or target structure. A barrier can be, for example, bone, skin, blood, cells, tissue, plastic, glass, or other composition.

Use of Mechanophores Linked to a Gel or Elastomer Matrix to Trigger an Optogenetic Response Gel or elastomer matrices containing mechanophores can be triggered by HIFU to emit light, which can be used to control or affect a target structure. A target structure or a targeted structure can be, e.g., cells, sub-populations of cells, cells in culture, tissue in culture, or cells, tissues, or organs within a host (e.g., a mammal, such as a human). One or more cells or cell types of a targeted structure can be genetically modified to express a light sensitive protein.

A light emission or chromogenic change can be triggered from a gel or elastomer matrix as described herein by subjecting the composition to high intensity focused ultrasound such that a light emission or chromogenic change is produced from the mechanophore within the gel or elastomer matrix.

In an embodiment, a mechanophore covalently linked to a gel or elastomer can be remotely and non-invasively activated. An activated mechanophore can emit light or exhibits a color change. Remotely means from a distance and without physical contact. A gel or elastomer matrix as described herein can be implanted within a cell, next to cells, within cell culture, within tissue, or within a patient or can be contacted with a cell, cell culture, tissue, or a patient (e.g., a mammal such as a human). High intensity focused ultrasound can be directed to the gel or elastomer matrix, or cell, cell culture, tissue, or patient such that the mechanophore is activated. No significant thermal increases are caused by the high intensity focused ultrasound. The activation can be a light emission or a chromogenic change. The target structure (e.g., cell, cell culture, tissue, or patient) can comprise one or more genetically modified cells, wherein the genetically modified cells express one or more recombinant light sensitive proteins. Alternatively or additionally, the gel or elastomer matrix can comprise one or more genetically modified cells, wherein the genetically modified cells express one or more recombinant light sensitive proteins In an embodiment, a method of triggering a change in a biological activity of a cell or tissue in vitro or in vivo is provided. The method comprises contacting a composition comprising a luminescent mechanophore covalently linked to a gel or elastomer matrix, wherein the chromogenic or luminescent mechanophore is present in the gel or elastomer matrix at about 1.0 wt % to about 5 wt %, with the cell or tissue or bringing the composition into the vicinity of the cell or tissue, and subjecting the composition to high intensity focused ultrasound such that a light emission or chromogenic change is produced from the mechanophore, wherein the light emission or chromogenic change triggers a change in the biological activity of the cell or tissue.

In an embodiment a method for remotely and non-invasively activating a mechanophore in the vicinity of a cell, cell culture, tissue, or patient is provided. The method comprises implanting a composition comprising a luminescent mechanophore covalently linked to a gel or elastomer matrix, wherein the chromogenic or luminescent mechanophore is present in the gel or elastomer matrix at about 1.0 wt % to about 5 wt %, within a cell, cell culture, tissue, or patient; contacting the composition with a cell, cell culture, tissue, or patient; or bringing the composition into the vicinity a cell, cell culture, tissue, or patient, and directing high intensity focused ultrasound to the composition such that the mechanophore is activated. The method of activation can be done in vivo or in vitro.

An embodiment provides a method for illuminating a targeted structure of a cell, tissue, or patient comprising a light sensitive protein. The method comprises: contacting or bringing into the vicinity of the cell, tissue, or patient a composition comprising a luminescent mechanophore covalently linked to a gel or elastomer matrix, wherein the chromogenic or luminescent mechanophore is present in the gel or elastomer matrix at about 1.0 wt % to about 5 wt %, and directing high intensity focused ultrasound to the composition such that the mechanophore is activated and illumines a targeted structure of a cell, tissue, or patient. The method of illumination can be done in vivo or in vitro.

In an embodiment genetically modified cells are present within, adjacent to, or within the vicinity (e.g., within about 0.0, 0.0001, 0.001, 0.01, 0.05, 0.1, 0.5, 1.0, 1.5, 2.0, 3.0, 4.0 mm or more or within about 4.0, 3.0, 2.0, 1.5, 1.0, 0.5, 0.1, 0.05, 0.01, 0.001, 0.0001 mm, or less) of a target structure. The genetically modified cells can be part of the target structure (e.g., cells in culture or cells within an organism or patient).

Genetically modified and genetically non-modified cells described herein can be e.g., neurons, stem cells, red blood cells, white blood cells, neutrophils, eosinophils, basophils, lymphocytes, platelets, nerve cells, neuroglial cells, muscle cells, skeletal muscle cells, cardiac muscle cells, atrial cells, ventricular cells, Prukinje cells, smooth muscle cells, cartilage cells, bone cells, osteoclasts, osteoblasts, osteocytes, lining cells, skin cells, endothelial cells, epithelial cells, fat cells, cancer cells, bacterial cells, or virus-infected cells.

Tissues include, for example, connective tissue (e.g., fat tissues, bone, tendon), muscle tissue (e.g., cardiac muscle tissue, smooth muscle tissue, skeletal muscle tissue), nervous tissue (e.g., brain tissue, spinal cord tissue, nerve tissue), and epithelial tissue (e.g. skin, simple squamous, simple cuboidal, simple columnar, pseudostratified columnar, stratified squamous keratinized, stratified squamous non-keratinized). One of more cells or cell sub-types can be genetically modified to express a light sensitive protein.

Other cells and tissues that can targeted include for example, joint, ligaments, tendons, glands, stomach, intestine, liver, gall bladder, pancreas, lungs, kidney, bladder, urethra, ovary, uterus, testes, prostate, heart, arteries, veins, lymph node, bone marrow, spleen, spinal cord, a nerve cell body, a ganglion, a dorsal root ganglion, an afferent nerve fiber, an afferent nerve bundle, an afferent nerve ending, a sensory nerve fiber, a sensory nerve bundle, a sensory nerve ending, and a sensory receptor.

The compositions described herein can be used for affecting a change in biological activity to a target structure (e.g., cells, tissues, or a patient). For example, a gel or elastomer matrix as described herein can be provided in the vicinity of or contacted with a target structure. HIFU can be applied to the gel or elastomer matrix and/or target structure such that one or more biological responses are activated in the target structure. A target structure is activated when it exhibits a change (i.e., a change in biological activity or biological response) when exposed to light emission or chromogenic change from an activated mechanophore.

A change in biological activity or biological response can comprise, for example, modifying the target structure, modulating the biological activity of the target structure, activating psoralen, generating a reactive oxygen species, photo activating a drug, sterilizing the target structure, inducing an autoimmune response, exciting a DNA strand of a cancer cell, redirecting a metabolic pathway, up-regulating genes, down-regulating genes, secreting cytokines, altering cytokine receptor responses, releasing metabolites, bonding a pharmaceutical agent to a cellular structure (e.g., nuclear DNA, mRNA, rRNA, ribosome, or mitochondrial DNA), altering a cellular response or a metabolic rate of the target structure, emitting ultraviolet light (e.g., to act as a germicide), emitting near infrared light (e.g., to act as an anti-inflammatory agent, to promote cellular proliferation, to reduce pain), heating a local area of the target structure, or combinations thereof.

A target structure can be contacted with one or more activatable pharmaceutical agents that are capable of effecting a change in the target structure when activated with the light.

A target structure can be, for example, a tissue, eukaryotic cell, a prokaryotic cell, a subcellular structure such as a cell membrane, a nuclear membrane, cell nucleus, nucleic acid, mitochondria, ribosome, or other cellular organelle or component. A target structure can be an extracellular structure. A target structure can be a virus or prion.

An activation or change in biological activity of a target structure can be destruction, lysis, or inactivation of the target structure. Alternatively, the activation or change does not result in destruction or inactivation of the target structure. In an embodiment, the change in biological activity enhances an activity of the target structure.

An activation or change in biological activity or a target structure can result in the treatment of a condition, disorder, or disease in the subject, cell, or tissue. A condition, disorder, or disease can be, for example, cancer. The condition, disorder, or disease can occur in a soft tissue, cartilage, bone, or combinations thereof. The condition, disorder or disease can be, for example, chronic pain, an autoimmune disease, prion infection, viral infection, bacterial infection, fungal infection, parasitic infection, varicose veins, enlarged prostate, retinal injuries, other ocular diseases, Parkinson's disease, behavioral, perceptional and/or cognitive disorder. A change in biological activity can be, for example, wound healing, enhancement of tissue growth, nerve regeneration or sensory regeneration/restoration.

A change in biological activity or activation of target structure can comprise reduction or removal of adipose cells or tissue or modulation of cell death, modulation of cell growth and division, modulation of an activity, quantity, or number of intracellular components in a cell, modulation of an activity, quantity, or number of extracellular components produced by, excreted by, or associated with a cell.

A change in biological activity or activation of a target structure can comprise, e.g., stimulation or modulation of brain cell activity with light.

A change in biological activity or activation of a target structure can modify the target structure and can modulate the biological activity of the target structure thus treating a condition, disorder or disease affecting the target structure. The condition, disorder, or disease can be mediated by abnormal cellular proliferation and the change in biological activity can ameliorates the abnormal cellular proliferation.

The condition, disorder, or disease can be, for example, cardiac ablation, photoangioplastic conditions, intimal hyperplasia, arteriovenous fistula, macular degeneration, psoriasis, acne, hopecia areata, portwine spots, hair removal, autoimmune diseases, rheumatoid and inflammatory arthritis, behavioral and cognitive disorders/conditions, joint conditions, Parkinson's disease, retinal injuries and other ocular diseases, enlarged prostate, varicose veins, reduction or removal of fat deposits (liposuction), nerve regeneration, sensory regeneration/restoration, wound healing, chronic pain, conditions occurring in bone tissue, conditions occurring in a soft tissue and/or cartilage, and lymph node conditions.

The light emission from an activated mechanophore can act on a pharmaceutical agent that is photoactivatable, such as psoralens, pyrene cholesteryloleate, acridine, porphyrin, fluorescein, rhodamine, 16-diazorcortisone, ethidium, transition metal complexes of bleomycin, transition metal complexes of deglycobleomycin organoplatinum complexes, alloxazines, vitamin Ks, vitamin L, vitamin metabolites, vitamin precursors, naphthoquinones, naphthalenes, naphthols and derivatives thereof having planar molecular conformations, porphorinporphyrins, dyes and phenothiazine derivatives, coumarins, quinolones, quinones, anthroquinones, 8-MOP, AMT, 7,8-dimethyl-10-ribityl, isoalloxazine, 7,8,10-trimethylisoalloxazine, 7,8-dimethylalloxazine, isoalloxazine-adenine dinucleotide, alloxazine mononucleotide, aluminum (III) phthalocyanine tetrasulonate, hematophorphyrin, and phthadocyanine.

The pharmaceutical agent can be coupled to a carrier that is capable of binding to a receptor site on or near the target structure. The carrier can be, for example, insulin, interleukin, thymopoietin or transferrin. A pharmaceutical agent can be coupled to the carrier by a covalent bond or a non-covalent bond. A receptor site can be, for example, nucleic acids of nucleated cells, antigenic sites on nucleated cells, or epitopes.

A pharmaceutical agent can be, for example, a DNA intercalator or a halogenated derivative thereof, a light-sensitive protein that upon exposure to light emission from a mechanophore modulates, for example, a signaling event in the brain.

A pharmaceutical agent can be present in a gel or elastomer matrix or can be delivered to the target structure separately.

In an embodiment, the compositions and methods described herein can be used to treat various diseases. For example, a viral vector carrying a light sensitive protein (e.g., NpHR) under the control of a promoter that is active in the principal neurons of the hippocampus (e.g. a CaMKIIα promoter) can be delivered to those neurons in vivo or in vitro such that the neurons are genetically modified to express NpHR. A gel or elastomer matrix described herein can be delivered to the vicinity of the neurons and activated with HIFU. Activated NpHR can hyperpolarize the principal neurons of the hippocampus and inhibit epileptiform activity. In an alternative embodiment, a gel or elastomer matrix described herein can include genetically modified cells that express NpHR. The gel or elastomer matrix can be delivered to the vicinity of the neurons and then activated with HIFU. The activated NpHR can hyperpolarize the principal neurons of the hippocampus and inhibit epileptiform activity.

In another example, a viral vector (e.g., AAV) carrying a light sensitive protein (e.g., enhanced halorhodopsin (eNpHR3.0)) under the control of a promoter that is active in hippocampal pyramidal cells can be delivered to those cells in vivo or in vitro such that the cells are genetically modified to express eNpHR3.0. A gel or elastomer matrix described herein can be delivered to the vicinity of the cells and activated with HIFU. Activated eNpHR3.0 can hinder the electrographic and behavioral onset of seizure activity. In an alternative embodiment, a gel or elastomer matrix described herein can include genetically modified cells that express eNpHR3.0. The gel or elastomer matrix can be delivered to the vicinity of the cells and then activated with HIFU. The activated eNpHR3.0 can hyperpolarize the hippocampal pyramidal cells and inhibit epileptiform activity.

In another example, a viral vector (e.g., AAV-5) carrying a light sensitive protein (e.g., ChR2) under the control of a promoter that is active in the deep/intermediate layers of the superior colliculus (DLSC) can be delivered using, for example, microinjection, to the DLSC in vivo or in vitro such that the cells of the DLSC are genetically modified to express ChR2. A gel or elastomer matrix described herein can be delivered to the vicinity of the cells and activated with HIFU. Activation of the DLSC with ChR2 can exert broad-spectrum anticonvulsant actions and attenuate seizures. In an alternative embodiment, a gel or elastomer matrix described herein can include genetically modified cells that express ChR2. The gel or elastomer matrix can be delivered to the vicinity of the cells and then activated with HIFU. Activation of the DLSC with ChR2 can exert broad-spectrum anticonvulsant actions and attenuate seizures.

In another example, a viral vector carrying a light sensitive protein (e.g., ChR2) under the control of a promoter (e.g., Thy1) that is active in the ipsilesional primary motor cortex (iM1) can be delivered to the iM1 in vivo or in vitro such that the cells of the iM1 are genetically modified to express ChR2. A gel or elastomer matrix described herein can be delivered to the vicinity of the cells and activated with HIFU. The cells of the iM1 are stimulated and can, e.g., improve stroke recovery. In an alternative embodiment, a gel or elastomer matrix described herein can include genetically modified cells that express ChR2. The gel or elastomer matrix can be delivered to the vicinity of the iM1 cells and then activated with HIFU. Activation of the iM1 with ChR2 can, e.g., improve stroke recovery.

In another example, a light sensitive protein (e.g., ChR2) can be delivered to cardiomyocytes and upon activation can produce an inward current sufficient to elicit an action potential. A light sensitive protein (e.g., an excitatory opsin) can be delivered to cardiac tissue by, e.g., direct modification of some or all cardiomyocytes or through cell delivery. That is, the introduction of opsin expressing cells (e.g., stem cells or fibroblasts) that can couple with native cardiomyocytes through gap junctions. Opsin-expressing cells or viruses can be directly injected or perfused into heart tissues. A tandem-cell-unit approach (TCU) can be used where donor cells expressing a light sensitive protein (e.g., ChR2) electrically couple to cardiomyocytes through gap junctions to confer optical sensitivity to the syncytium. A gel or elastomer matrix as described herein can be delivered to the vicinity of the cardiomyocytes. The cardiomyocytes can then be activated using HIFU targeting the gel or elastomer matrix. The pacing of the cardiomyocytes can be controlled though the activation.

The compositions and methods are more particularly described below and the Examples set forth herein are intended as illustrative only, as numerous modifications and variations therein will be apparent to those skilled in the art. As used in the description herein and throughout the claims that follow, the meaning of "a", "an", and "the" includes plural reference unless the context clearly dictates otherwise. The term "about" in association with a numerical value means that the value varies up or down by 5%. For example, for a value of about 100, means 95 to 105 (or any value between 95 and 105).

The terms used in the specification generally have their ordinary meanings in the art, within the context of the compositions and methods described herein, and in the specific context where each term is used. Some terms have been more specifically defined below to provide additional guidance to the practitioner regarding the description of the compositions and methods.

All patents, patent applications, and other scientific or technical writings referred to anywhere herein are incorporated by reference herein in their entirety. The embodiments illustratively described herein suitably can be practiced in the absence of any element or elements, limitation or limitations that are specifically or not specifically disclosed herein. Thus, for example, in each instance herein any of the terms "comprising", "consisting essentially of", and "consisting of" may be replaced with either of the other two terms, while retaining their ordinary meanings. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by embodiments, optional features, modification and variation of the concepts herein disclosed may be resorted to by those skilled in the art, and that such modifications and variations are considered to be within the scope of this invention as defined by the description and the appended claims.

Whenever a range is given in the specification, for example, a temperature range, a time range, or a composition or concentration range, all intermediate ranges and subranges, as well as all individual values included in the ranges given are intended to be included in the disclosure. It will be understood that any subranges or individual values in a range or subrange that are included in the description herein can be excluded from the aspects herein. It will be understood that any elements or steps that are included in the description herein can be excluded from the claimed compositions or methods In addition, where features or aspects of the invention are described in terms of Markush groups or other grouping of alternatives, those skilled in the art will recognize that the invention is also thereby described in terms of any individual member or subgroup of members of the Markush group or other group.

The following are provided for exemplification purposes only and are not intended to limit the scope of the invention described in broad terms above.

EXAMPLES

The ability of HIFU to trigger polymer mechanochemistry in a gel or elastomer matrix via solid-state mechanical deformation is demonstrated herein. HIFU can spatiotemporally control acoustic pressure and target specific volumes. Described herein, with working examples, are HIFU setups that can induce mechanophore activation with moderate stress and short sonication duration. The output pressure of HIFU systems for different excitations can be calibrated using a hydrophone and correlated to the onset of mechanochemical activation. A mechanophore covalently crosslinked into a gel or elastomer matrix can undergo electrocyclic ring-opening under acoustic pressure and generate a deep-orange colored merocyanine. Also demonstrated is the activation of a mechanoluminescent mechanophore, which under force generates an excited ketone species that can be harvested by an energy acceptor to emit light.

Example 1. Materials and Methods

A. General Synthetic Methods. All reactions were carried out in oven- or flame-dried glassware, under an atmosphere of dry $N_2$ unless otherwise indicated. Organic reagents were purchased from Sigma-Aldrich, Fisher Scientific or Acros Organics and used as received. Solvents were purchased as anhydrous grade or dried by passing through an activated alumina column on an Innovative Technology PureSolv solvent purification system. Thin layer chromatography was performed with silica gel-coated aluminum plates (Fluka, with fluorescent indicator) and visualized under UV light or with iodine staining. Flash chromatography was performed with 230-400 mesh silica gel (Silicycle SiliaFlash P60) or using a Biotage Isolera system with SiliaSep Flash cartridges. Routine NMR spectra were obtained on Varian spectrometers (500 MHz Inova). $^1H$ and $^{13}C$ spectra were referenced to residual solvent signal relative to trimethylsilane. High resolution mass spectrometry was performed on a Waters Q-Tof Ultima using electrospray ionization. Mechanophores were synthesized according to the literature: NP was prepared as previously described (Caruso M M, et al. (2009) Mechanically-induced chemical changes in polymeric materials. *Chem Rev* 109 (11):5755-5798) and recrystallized from chloroform/ethanol before use. Dioxetane was prepared as previously described (Li J, Nagamani C, Moore J S (2015) Polymer mechanochemistry: from destructive to productive. *Acc Chem Res* 48 (8):2181-2190). A Bruker D8 Venture Duo diffractometer using a Cu source was used to collect X-ray diffraction data on NP single crystals. See Table 1 for structure refinement details.

TABLE 1

Structure Refinement Details for the NP Mechanophore

| | |
|---|---|
| Identification code | dd34nsa |
| CCDC Number | 1890871 |
| Empirical formula | O37 H34 O6 |
| Formula weight | 574.64 |
| Temperature | 200(2) K |
| Wavelength | 1.54178 Å |
| Crystal system | Monoclinic |
| Space group | P2$_1$ |
| Unit cell dimensions | a = 12.6780(3) Å  a = 900 |
| | b = 8.3614(2) Å  b = 105.3502(8)° |
| | c = 14.8699(4) Å  g = 90° |
| Volume | 1520.06(7) A3 |
| Z | 2 |
| Density (calculated) | 1.255 Mg/m3 |
| Absorption coefficient | 0.681 mm$^{-1}$ |
| F(000) | 608 |
| Crystal size | 0.368 × 0.257 × 0.130 mm3 |
| Theta range for data collection | 3.615 to 68.435° |
| Index ranges | -15 <= h <= 15, -10 <= k <= 10, -17 <= l <= 17 |
| Reflections collected | 23941 |
| Independent reflections | 5556 [R(int) =0.0321] |
| Completeness to theta = 67.679° | 99.9% |
| Absorption correction | Integration |
| Max. and min. transmission | 0.9599 and 0.8294 |
| Refinement method | Full-matrix least-squares on F$^2$ |
| Data/restraints/parameters | 5556/203/470 |
| Goodness-of-fit on F$^2$ | 1.064 |
| Final R indices [l > 2sigma(l)] | R1 = 0.0321, wR2 = 0.0785 |
| R indices (all data) | R1 = 0.0333, wR2 = 0.0796 |
| Absolute structure parameter | 0.39(19) |
| Extinction coefficient | 0.0224(11) |
| Largest diff. peak and hole | 0.267 and -0.160 e · Å$^{-3}$ |

B. Preparation of PDMS with NP or NP-control.

The chromogenic PDMS samples contain 1.5 wt % of the vinyl-terminated naphthopyran, covalently incorporated into the elastomeric network, and were prepared using a Sylgard 184 kit. In a typical procedure, NP (160 mg) was dissolved in 300 μL of xylenes in a 15 mL polypropylene conical tube. Sylgard 184 pre-polymer base (9.57 g) was added and the mixture stirred briefly and then vigorously mixed by vortex. The Sylgard 184 curing agent (950 mg) was then added and vigorously mixed until a homogenous off-white consistency was obtained. The mixture was poured onto a 50 mm diameter Teflon-lined petri dish, and air bubbles removed by placing under high vacuum for 2 h. The pre-polymer was oven-cured at 65° C. overnight to form transparent films that peeled cleanly from the mold. The hemisphere-shaped samples were cast in a 40 mm diameter hollow ball (Stiga, 1-Star Table Tennis Ball), which was peeled off after curing.

C. Preparation of PDMS with 1,2-dioxetane or 1,2-dioxetane control. The mechanoluminescent PDMS samples contain 1.5 wt % of the vinyl-terminated 1,2-dioxetane and 0.5 wt % of 9,10-diphenylanthracene (DPA) as a fluorescent energy harvester. The 1,2-dioxetane (30 mg) and DPA (10 mg) were dissolved in 200 μL of xylenes and passed through a 0.45 μm syringe filter into a 20 mL scintillation vial. Sylgard 184 pre-polymer base (1.95 g) was added, and then the mixture mixed vigorously. Some precipitation of DPA is observed. Sylgard 184 curing agent (195 mg) was then added and the vial vortexed until thoroughly incorporated. The mixture was poured into a 50 mm diameter Teflon-coated petri dish, placed under high vacuum for 2 hours, then cured at 65° C. overnight.

For the 3 mm thick films, a donut-shaped film of unfunctionalized PDMS (prepared from a 10:1 w/w mixture of Sylgard 184 pre-polymer base and curing agent and cured at 65° C. for 3 hours after degassing under vacuum) was first made in a 50 mm diameter Teflon-coated petri dish with a 2.5 mm diameter Teflon cylinder placed in the center to create a void. The Teflon cylinder was then removed and the void filled with the Sylgard 184 mixture containing 1,2-dioxetane and DPA, and the whole sample degassed and then oven-cured at 65° C. overnight. The samples containing non-functionalized dioxetane at 1.5 wt % and 0.5 wt % 9,10-diphenylanthracene were also prepared in the same manner.

Synthesis of Vinyl-Terminated Dioxetane

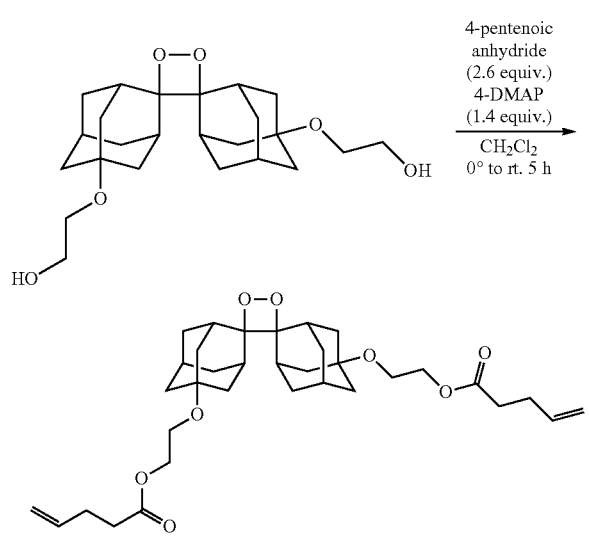

5'/7'-bispent-4-enoate-5,5'/7'-dihydroxyethylenoxy-adamantylideneadamantane 1,2-dioxetane was synthesized as described by Clough et al. (2016) Covalent bond scission in the mullins effect of a filled elastomer: real-time visualization with mechanoluminescence. *Adv Funct Mater* 26 (48): 9063-9074. $^1$H NMR (500 MHz, CDCl$_3$) δ 5.94-5.72 (m, 2H), 5.17-4.92 (m, 4H), 4.23-4.09 (m, 2H), 3.59 (dt, J=25.8, 5.0 Hz, 2H), 2.83 (s, 1H), 2.63 (s, 1H), 2.54-1.02 (m, 7H). $^{13}$C NMR (125 MHz, CDCl$_3$) δ 178.35, 173.21, 136.77, 136.48, 132.24, 115.74, 115.58, 94.02, 72.64, 72.52, 71.72, 71.66, 71.28, 71.10, 64.46, 64.35, 64.26, 64.19, 64.08, 59.21, 58.65, 58.43, 46.86, 42.53, 41.47, 41.22, 41.09, 40.36, 38.56, 38.46, 38.38, 36.23, 36.08, 34.14, 34.10, 33.72, 33.57, 33.56, 33.46, 33.32, 31.67, 30.89, 29.64, 28.90, 28.85, 28.63, 21.04. HRMS (ESI): [M+H$^+$] calculated m/z=585.3422 for C$_{34}$H$_{49}$O$_8^+$, found 585.3411.

Synthesis of Non-Functionalized Dioxetane Control

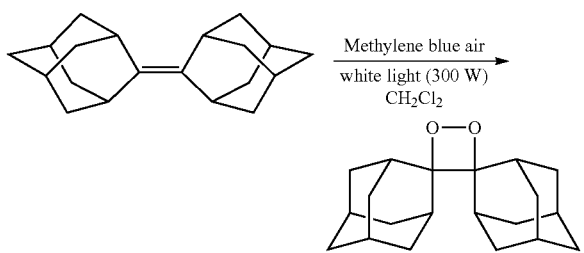

Synthesis of adamantylideneadamantane peroxide was adapted from Clough et al. (2016) Covalent bond scission in the mullins effect of a filled elastomer: real-time visualization with mechanoluminescence. *Adv Funct Mater* 26 (48): 9063-9074. $^1$H NMR (500 MHz, CDCl$_3$) δ 5.30 (s, 6H), 3.48 (q, J=7.0 Hz, 2H), 2.90 (t, J=3.1 Hz, 1H), 2.01-1.78 (m, 6H), 1.69 (t, J=13.3 Hz, 3H), 1.58 (s, 1H), 1.33-1.17 (m, 5H), 0.91-0.81 (m, 2H). $^{13}$C NMR (125 MHz, CDCl$_3$) δ 204.17, 95.96, 47.11, 39.78, 39.40, 37.55, 37.51, 37.41, 36.98, 35.30, 34.78, 32.93, 32.04, 31.99, 31.85, 29.84, 28.71, 27.59, 27.38, 27.34, 26.87, 26.67, 22.84, 14.27. HRMS (ESI): [M+Na$^+$] calculated m/z=323.1982 for C$_{20}$H$_{28}$O$_2$Na$^+$, found 323.1988.

The mechanoluminescent PDMS samples contain 1.5 wt % of the vinyl-terminated 1,2-dioxetane and 0.5 wt % of 9,10-diphenylanthracene (DPA) as a fluorescent energy harvester. The 1,2-dioxetane (30 mg) and DPA (10 mg) were dissolved in 200 μL of xylenes and passed through a 0.45 μm syringe filter into a 20 mL scintillation vial. Sylgard 184 pre-polymer base (1.95 g) was added, and then the mixture mixed vigorously. Some precipitation of DPA is observed. Sylgard 184 curing agent (195 mg) was then added and the vial vortexed until thoroughly incorporated. The mixture was poured into a 50 mm diameter Teflon-coated petri dish, placed under high vacuum for 2 hours, then cured at 65° C. overnight. For the 3 mm thick films, a donut-shaped film of unfunctionalized PDMS (prepared from a 10:1 w/w mixture of Sylgard 184 pre-polymer base and curing agent and cured at 65° C. for 3 hours after degassing under vacuum) was first made in a 50 mm diameter Teflon-coated petri dish with a 2.5 mm diameter Teflon cylinder placed in the center to create a void. The Teflon cylinder was then removed and the void filled with the Sylgard 184 mixture containing 1,2-dioxetane and DPA, and the whole sample degassed and then oven-cured at 65° C. overnight.

D. HIFU Triggering System.

The HIFU setup comprises a function generator, spherically-focused piezoelectric transducers (FUS Instruments, Canada) centered at 550 kHz and 1 MHz, a power amplifier (FUS Instruments, Canada), a low pass filter (10 MHz), and an impedance matching box. The input signal generated by the function generator was increased as much as 30 dB using a power amplifier and fed to the transducer through a low pass filter (10 MHz) and an impedance matching box. The entire setup was synchronized with the computer programmed to automatically control the input parameters in the function generator and the sonication time.

A HIFU-based triggering system was based on two aspects: one is boundary condition of the sample-holder assembly; and the other is the ability to spatiotemporal control the mechanochemical activation. For the boundary condition, two ring-shaped polycarbonate plates were used to circumferentially hold the PDMS samples. There is no substrate in the longitudinal direction that causes the reflection of the pressure field. In this configuration, the size of the beamwidth becomes one order of magnitude smaller than that of the sample (with the ratio of 0.05), ensuring the stress development on the focal spot without significant geometric interventions. This enables a better understanding of the relationship between the HIFU-induced pressure and the mechanophore activation. With this boundary condition, the acoustic pressure applied at the focal spot was estimated. Spatial control of HIFU irradiation was achieved using a computer-controlled micro-positioning system, which allowed the positioning of the sample-holder assembly at the focal distance with 2 μm spatial accuracy. The sample-holder assembly was mounted onto the positioning system and precisely placed at the focal distance of the transducer with its face (y-z direction) perpendicular to the beam of the transducer. In order to control acoustic pressure in the setup, input voltage set in the function generator to the HIFU transducer was first calibrated with the output voltage of the beam at the focal point, and then the conversion of the peak-to-peak amplitude of the output voltage to the acoustic pressure was achieved with the hydrophone sensitivity. With this procedure, the acoustic pressure at the focus was estimated. Based on this, the HIFU-triggering system generates the targeted pressure at the focus during the operation period, and thus the mechanical force was transferred into the PDMS samples.

Example 2. Design of Mechanoactive Polymer and HIFU-based Triggering System

Figure 6:
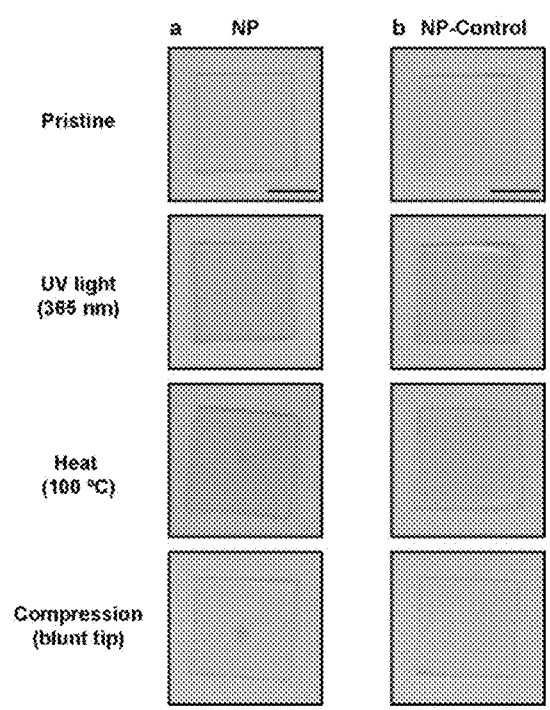
FIG. 6 shows photographs of PDMS films covalently functionalized with either NP (a) or NP-control (b) in response to external stimuli. Both NP and NP-control films are photo- and thermochromic; only the NP-containing film is mechanochromic, with localized color change at the site of compression by a blunt-tipped stylus. Scale bar=5 mm.

Crosslinked PDMS elastomer was used as a bulk matrix to investigate HIFU-triggered polymer mechanochemistry due to the biocompatibility of the material as well as the ease of covalent functionalization via hydrosilylation to incorporate mechanophores. Naphthopyran-incorporated crosslinked elastomeric PDMS specimens were prepared as 1.5 and 5 mm-thick films according to Robb et al. (Regioisomer-specific mechanochromism of naphthopyran in polymeric materials. *J Am Chem Soc* (2016) 138 (38):12328-12331), using bisvinyl-terminated, mechanoactive NP (FIG. 1A) or the monovinyl NP-control, which is mechanically inactive and serves as a control (FIG. 1B). The hydrosilylation reaction covalently incorporates these naphthopyrans into the elastomer by crosslinking the PDMS matrix at the position of the vinyl handles. The molecular positions of the bisvinyl attachment points in the NP mechanophore effectively transmit mechanical force to the mechanophore's C—O pyran bond to drive electrocyclic ring-opening. On the other hand, the NP-control containing a single vinyl terminus does not experience significant molecular deformation when mechanical force is applied to the PDMS network (FIG. 1B). 1.5 mm-thick PDMS films functionalized with 1.5 wt % of NP (NP-PDMS) show color change under mechanical force, exerted by compression with a blunt-tipped stylus (FIG. 6). This color change is reversible under ambient conditions within 10 minutes. In contrast, the same mechanical stimulus does not result in observable color change with an identically prepared sample for which the NP-control is used in place of NP. Films of PDMS covalently functionalized with either NP or NP-control exhibit color change when irradiated with 365 nm UV light or when heated to 100° C., demonstrating photo- and thermochromism (FIG. 6).

Figure 2:
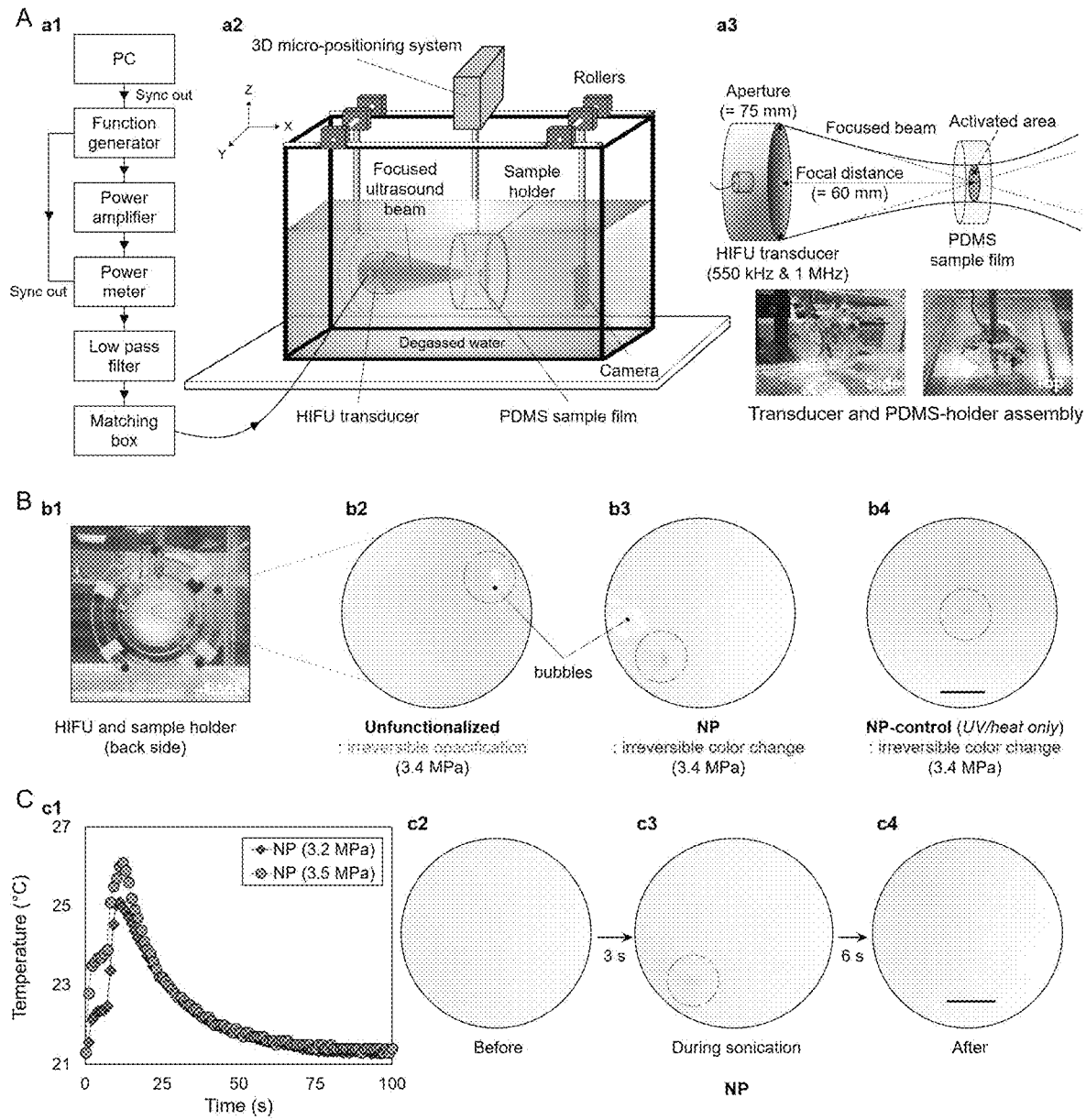
FIG. 2 shows HIFU-induced mechanochromic response of the NP-PDMS elastomer under 1 MHz continuous wave (sonication time of seven seconds): (A) (a1-a3) schematic of the experimental setup and characteristics of the HIFU transducer; (B) (b1-b4) irreversible material damage with thermal ablation (unfunctionalized PDMS and NP) and example of thermally-induced activation at 3.4 MPa (NP-control); (C) (c1-c4) temperature (averaged) increase during the HIFU irradiation (3.2 MPa vs 3.5 MPa) and observed reversible color change in the NP-PDMS elastomer. Only mild temperature increases (ca. 4° C.) occur at the focal spot during sonication. Scale bar=2.5 mm.
Figure 7:
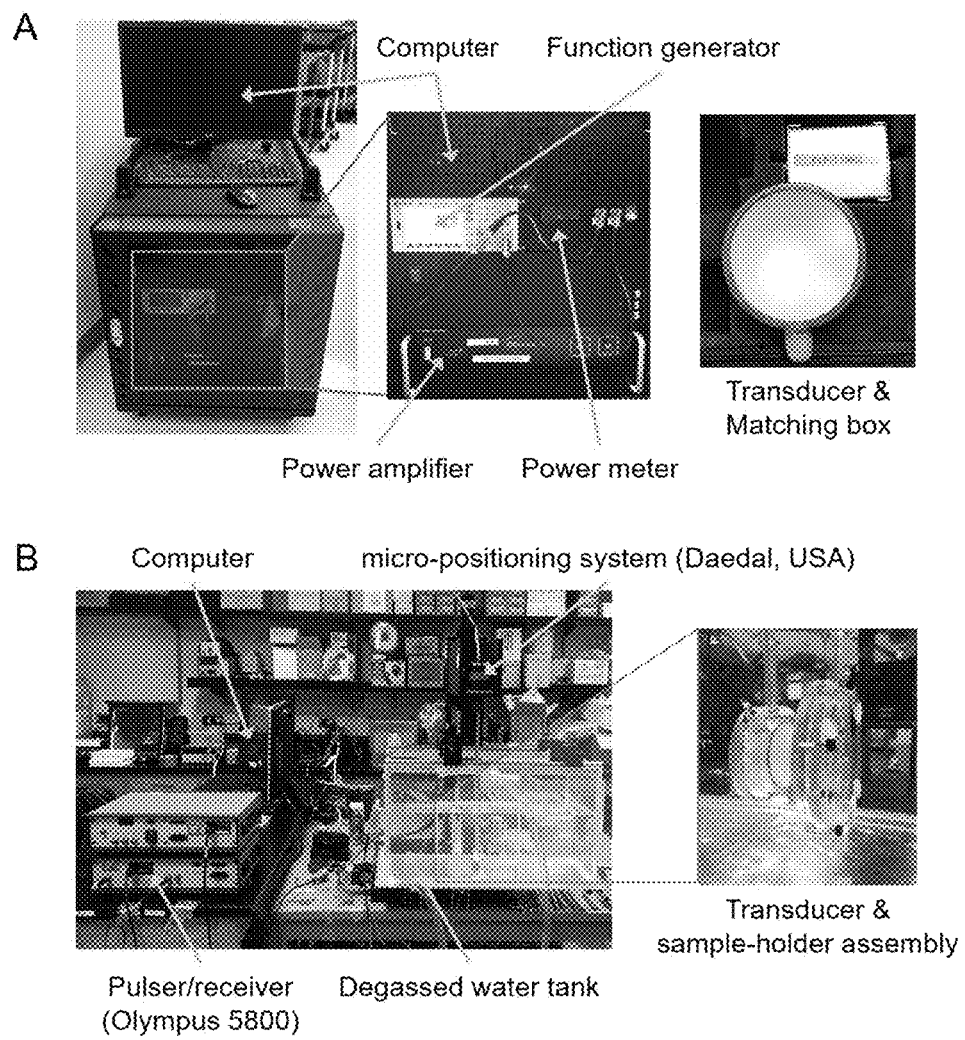
FIG. 7 shows a photograph of the (A) high-intensity focused ultrasound (HIFU) setup and (B) setup for the spatial control of mechanochemical transduction.

A HIFU-based triggering system is illustrated in FIG. 2A. Spatial control of mechanoactive response was achieved by using a computer-controlled micropositioning stage capable of locating the sample-holder assembly with 2 μm spatial accuracy (FIG. 7B). The irradiation of solid polymers with HIFU can result in local heating at the interior of the bulk material, which accumulates thermal energy upon prolonged sonication. The interaction of HIFU with PDMS was examined to determine the extent of thermal effects on the samples and thus the temporal resolution. A 1.5 mm-thick film of unfunctionalized PDMS (i.e., without any naphthopyran functionalization) was first irradiated with continuous wave (CW) ultrasound at a frequency of 1 MHz for five to seven seconds, and the spatial-peak temporal average intensity ($I_{SPTA}$) of the beam varied from 39.4 to 376 W·cm$^{-2}$ (peak acoustic pressure amplitude, 1.1 to 3.4 MPa). At intensities less than or equal to 354 W·cm$^{-2}$ (3.3 MPa), no change in the material was visually observed in the unfunctionalized PDMS film. However, upon irradiation at 376 W·cm$^{-2}$ (3.4 MPa), irreversible opacification of the film at the focal spot was observed (FIG. 2B, b2). In addition, the formation of small bubbles was observed near the focal spot, providing additional evidence of thermal ablation (FIG. 2B, b2). Similarly, when the NP-PDMS films were irradiated with CW-HIFU at intensities exceeding ca. 354 W·cm$^{-2}$, ablation of the material was observed, resulting in irreversible discoloration (orange) of the film accompanied by bubble formation at the focal spot (FIG. 2B, b3). Both observations indicate that a lower intensity (<376 W·cm$^{-2}$) is desirable in order to avoid thermal effects that mask the mechanochromic changes. During ultrasonic irradiation, a thermocouple was used to track the temperature increase in the focal region. Only minor increases in temperature (<6° C.) were observed at intensities below 354 W·cm$^{-2}$ (3.3 MPa) for seven seconds (FIG. 2C, c1). However, the intensity-temperature relationship indicated that the temperature development around the focal spot would be significant from 354 W·cm$^{-2}$ upwards, suggesting that thermal ablation would be more dominant than mechanical activation as evident from the irreversible material damage observed.

Synthesis of NP

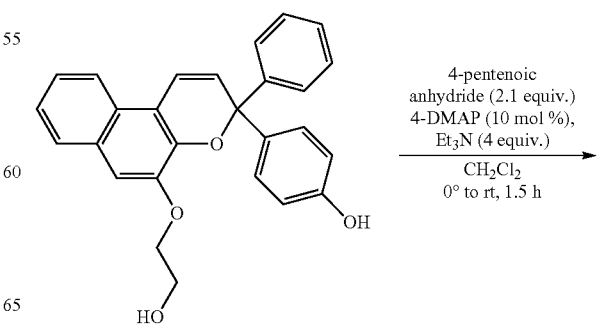

-continued

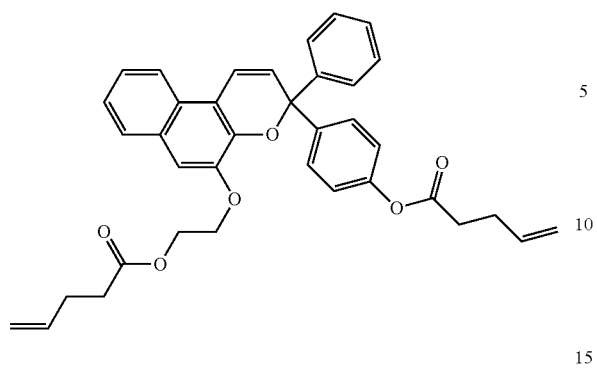

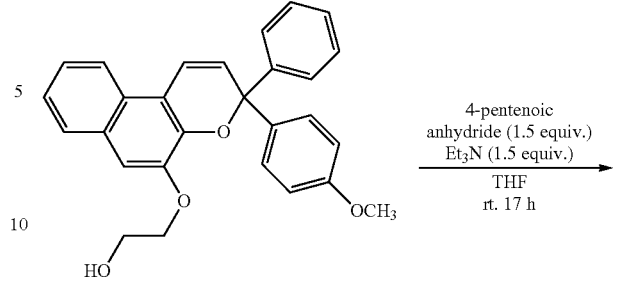

NP was prepared as previously described (Caruso M M, et al. (2009) Mechanically-induced chemical changes in polymeric materials. Chem Rev 109 (11):5755-5798) and recrystallized from chloroform/ethanol before use. NMR characterization matched the previous report, and the structure was further confirmed by x-ray crystallography (FIG. 11 with corresponding information in Table 1).

Synthesis of Monofunctional Control Naphthopyran (NP-control)

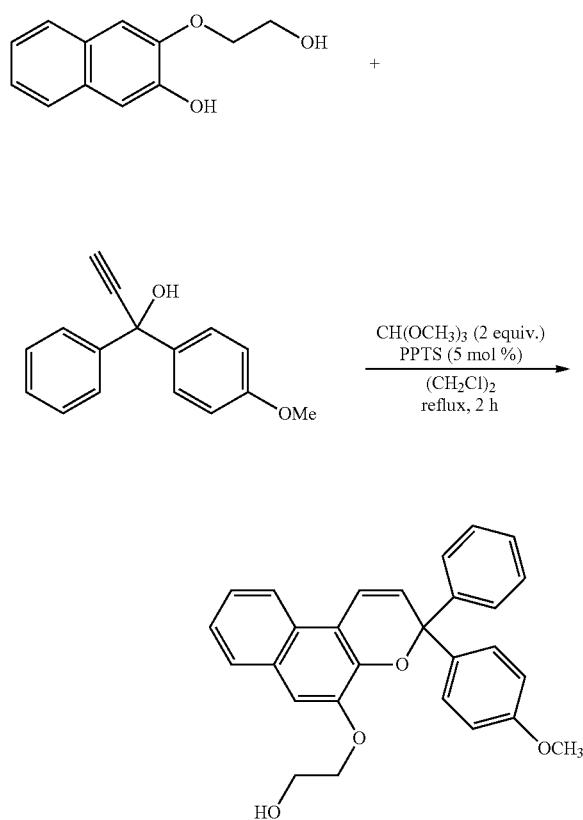

A flame-dried 100 mL round-bottom flask was charged with 3-(2-hydroxyethoxy) naphthalene-2-ol (743 mg, 3.64 mmol), 1-(4-methoxyphenyl)-1-phenylprop-2-yn-1-ol (953 mg, 4.0 mmol), and pyridinium p-toluenesulfonate (46.0 mg, 0.182 mmol).

Dichloroethane (20 mL) was added via syringe followed by trimethylorthoformate (773 mg, 797 μL, 7.28 mmol), and the homogeneous mixture was stirred at reflux for 2 h. After cooling to room temperature, the solvent was removed by evaporation under reduced pressure. Purification of the crude product by column chromatography ($SiO_2$, 15-50% EtOAc/hexanes) yielded the hydroxy-terminated naphthopyran as a red foam (1.02 g, 2.40 mmol, 66% yield). $^1$H NMR (500 MHz, Acetone-$d_6$) δ: 3.72 (s, 3H), 4.01 (q, J=5.1 Hz, 2H), 4.06 (bs, 1H), 4.27 (t, J=9.9 Hz, 2H), 6.55 (d, J=9.9 Hz, 1H), 6.83-6.86 (m, 2H), 7.23 (tt, J=7.4, 1.6 Hz, 1H), 7.28-7.35 (m, 5H), 7.43 (d, J=10.0 Hz, 1H), 7.49-7.52 (m, 2H), 7.60 (dt, J=8.4, 1.6 Hz, 2H), 7.69 (dd, J=8.2, 1.0 Hz, 1H), 7.96 (d, J=8.2 Hz, 1H). $^{13}$C NMR (125 MHz, Acetone-$d_6$) δ: 55.4, 61.3, 71.4, 82.8, 110.1, 114.1, 116.6, 120.4, 122.0, 125.0, 125.2, 125.9, 127.3, 127.98, 128.04, 128.8, 128.9, 130.1, 130.5, 137.7, 143.4, 146.1, 149.2, 159.9. HRMS (ESI): [M+H$^+$] calculated m/z=425.1747 for $C_{28}H_{25}O_4^+$, found 425.1773.

The hydroxyl-terminated naphthopyran (510 mg, 1.20 mmol) and 4-(dimethylamino) pyridine (49.0 mg, 0.4 mmol) were charged to a flame-dried 20 mL septum-capped vial. THF (15 mL) was added via syringe, followed by pentenoic anhydride (328 mg, 1.80 mmol) and triethylamine (153 mg, 210 μL, 1.80 mmol). The reaction was stirred for 17 h at room temperature, and then quenched by the addition of 1 mL of MeOH. After evaporation of solvent under reduced pressure, the crude product was purified by column chromatography ($SiO_2$, 0-30% EtOAc/hexanes) to give the monofunctional control naphthopyran as an orange gel, which solidified on standing (463 mg, 0.915 mmol, 76% yield). $^1$H NMR (500 MHz, Acetone-$d_6$) δ: 2.35 (q, J=6.4 Hz, 2H), 2.46 (t, J=7.1 Hz, 2H), 3.74 (s, 3H), 4.40-4.44 (m, 2H), 4.54-4.57 (m, 2H), 4.91-4.93 (m, 1H), 5.00-5.05 (m, 1H), 5.78-5.8 (m, 1H), 6.60 (d, J=9.9 Hz, 1H), 6.84-6.89 (m, 2H), 7.22-7.25 (m, 1H), 7.29-7.39 (m, 5H), 7.45 (d, J=9.9 Hz, 1H), 7.49-7.54 (m, 2H), 7.59-7.64 (m, 2H), 7.70 (d, J=8.1 Hz, 1H), 7.99 (d, J=8.5 Hz, 1H). $^{13}$C NMR (125 MHz, Acetone-$d_6$) δ: 29.5, 33.9, 55.4, 63.3, 67.7, 82.7, 110.2, 114.1, 115.7, 116.7, 120.4, 122.0, 125.0, 125.3, 126.0, 127.1, 128.1, 128.8, 120.0, 130.4, 137.7, 143.3, 146.2, 148.7, 159.9, 173.0. HRMS (ESI): [M+H$^+$] calculated m/z=507.2166 for $C_{33}H_{30}O_5^+$, found 507.2176.

Example 3. Acoustic Properties of PDMS Materials

Figure 11:
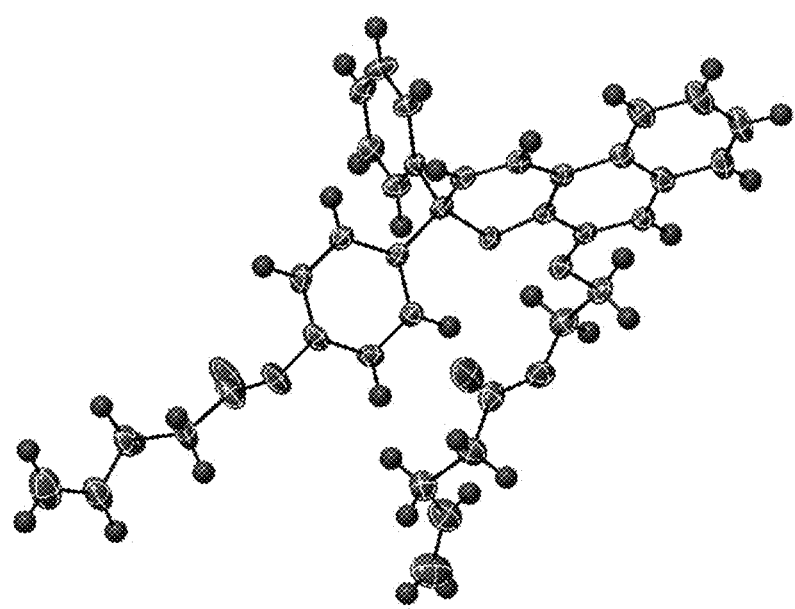
FIG. 11 shows molecular structure of the bisvinyl-terminated NP mechanophore refined from single crystal X-ray diffraction data. See Table 1 for refinement details.
Figure 12:
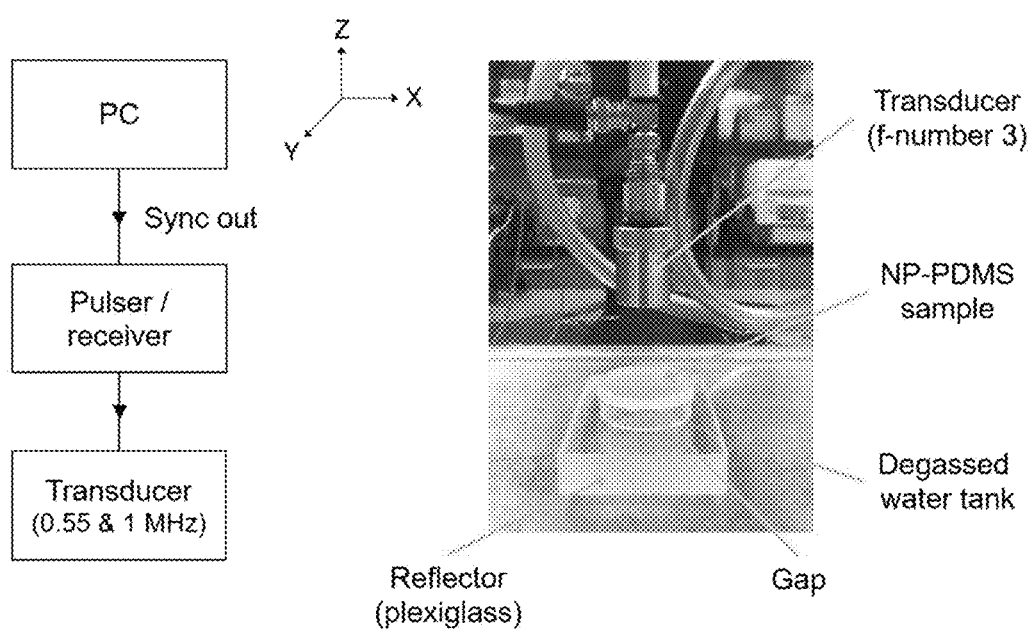
FIG. 12 shows Speed of sound and attenuation estimation. Attenuation coefficient, a is obtained from the log difference of the power spectrum from a reflector with and without NP-PDMS sample.

Acoustic properties of PDMS materials. To quantify the acoustic properties of the prepared NP-PDMS samples, speed of sound and attenuation were estimated using the methods introduced in Kemmerer J P, Oelze M L (2012) Ultrasonic assessment of thermal therapy in rat liver. *Ultrasound Med Biol* 38 (12):2130-2137. An Olympus 5800 pulser/receiver operated in pulse-echo mode with a pulse repetition frequency of 1 kHz, and the generated signal was fed to a single-element focused transducer (550 kHz or 1 MHz, f-number 3) aligned perpendicular to the sample in a degassed water bath (21±2° C.). Each transducer was positioned in front of the sample, respectively, at a distance of 5.7 cm, which is the nominal focal distance (FIG. 11). The reflected pulses from the top and bottom surfaces of a 5 mm thick flat NP-PDMS sample were averaged at least 100 times to increase signal-to-noise ratio (SNR) and recorded into a computer (FIG. 7B). Based on the time-of-flight (TOF) method, the speed of sound, c of the NP-PDMS was estimated by dividing the sample thickness by the time difference between the measured reflected signals. The averaged speed of sound in NP-PDMS was approximately 1170 m·s$^{-1}$. This estimated value is comparable to that of Sylgard 184 reported in the literature (Yuk H, et al. (2017) Hydraulic hydrogel actuators and robots optically and sonically camouflaged in water. *Nat Commun* 8:14230) suggesting that the mechanophore itself does not significantly affect the acoustic properties of PDMS. Using the measured density, ρ of the PDMS sample (=870 kg·m$^{-3}$), the acoustic impedance, $Z_o$ (=ρ·c) was calculated to be 1.02 MRayl (=MPa·s·m$^{-1}$). The attenuation coefficient, a (dB/cm) was estimated via a pulse-echo insertion loss method (Kemmerer J P, Oelze M L (2012) Ultrasonic assessment of thermal therapy in rat liver. *Ultrasound Med Biol* 38 (12):2130-2137):

$$a(f)=10\cdot(2d)^{-1}\cdot\log_{10}(P_r(f)\cdot P_s(f)^{-1}). \quad [3]$$

where $P_r(t)$ and $P_s(f)^{-1}$ ρ are the power spectrum of the reflected waveform from a reflector with and without the NP-PDMS samples, and d is the sample thickness.

The spectral log difference in Equation (1) has a linear trend within the effective bandwidth, which enables the estimation of the attenuation coefficient for each excitation frequency (1.60±0.04 dB·cm$^{-1}$ for 550 kHz and 2.05±0.04 dB·cm$^{-1}$ for 1 MHz). The measured acoustic and mechanical properties of the NP-PDMS are listed in Table 2.

TABLE 2

Acoustic parameters of PDMS with the NP mechanophore

| | |
|---|---|
| Speed of sound, c (m · s$^{-1}$) | 1169.3 |
| Acoustic impedance, $Z_o$ (MPa · s · m$^{-1}$) | 1.012 |
| Attenuation coefficient, a (dB · m$^{-1}$) | 160 (550 kHz) & 205 (1 MHz) |
| Density, ρ (kg · m$^{-3}$) | 865.8 |

Example 4. Development of HIFU-based Triggering System

HIFU triggering system and beam characteristics. A photograph of the custom HIFU setup for the mechanochemical transduction is provided in FIG. 7A. A function generator (33500B, Keysight Technologies, Santa Rosa, CA) was used to produce a sinusoidal voltage signal with a user-defined signal amplitude. The voltage signal was amplified through a radiofrequency power amplifier (NP Technologies Inc., Newbury Park, CA), a 10 MHz low pass filter and an impedance matching network before being sent to the spherically-focused HIFU transducer (FUS Instruments, Canada) with nominal center frequencies of 550 kHz and 1 MHz, respectively. Note that both HIFU transducers have a focal distance of 60 mm and diameter of 75 mm (f-number 0.8). The entire setup was synchronized with the computer programmed to automatically control the input parameters in the function generator and the sonication time. The sonication induced events were recorded using a waterproof digital camera with 1334×750-pixel resolution placed behind the PDMS films (FIG. 2A, a2).

Figure 10:
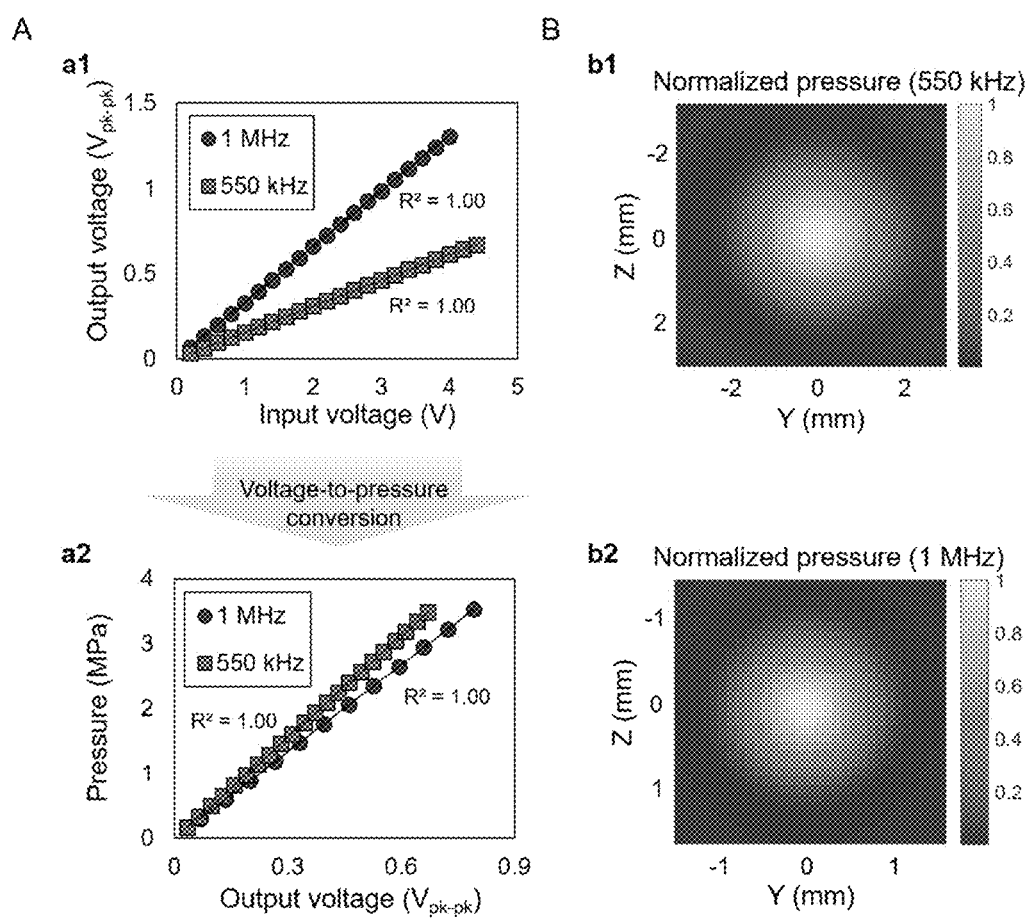
FIG. 10 shows calibration of HIFU setup: (A) (a1)-(a2) voltage-to-pressure conversion (the green square for 550 kHz and the blue circle for 1 MHz); and (B) (b1)-(b2) example of the obtained pressure profile (left: electric power=1.78 W, 550 kHz, and right: electric power=1.72 W, 1 MHz).

The spatial pressure distributions of each transducer (550 kHz and 1 MHz) were measured in a tank of degassed water using a fiber-optic hydrophone (10 μm active element, Precision Acoustics, Dorchester, UK) with a hydrophone step size of 100 μm in the y-z plane (FIG. 10B). The full width at half maximum (FWHM) beamwidth, $B_W$ and depth of field, $Z_F$ of each transducer were measured to be: 1.2 and 5.9 mm for 1 MHz; and 2.2 and 12.5 mm for 550 kHz, respectively. The output voltage signal measured with the hydrophone was converted to acoustic pressure using the hydrophone sensitivity interpolated from the data provided by the manufacturer (96.00 mV·MPa$^{-1}$ for 550 kHz and 112.04 mV·MPa$^{-1}$ for 1 MHz). The spatial-peak temporal average intensity ($I_{SPTA}$) was calculated by $$I_{SPTA}=p^2\cdot(2\cdot\rho\cdot c)^{-1} \quad [1]$$

where p is the peak acoustic pressure amplitude, ρ the density of material, and c the speed of sound. It is important to note that the intensity and pressure applied throughout the PDMS samples are slightly less than the estimated values due to reflection at the PDMS surface. The calculated pressure reflection coefficient is approximately −0.186, indicating that the intensity of the transmitted beam into the PDMS samples is decreased by 3.4%, e.g., from $I_{SPTA}$ of 333 W·cm$^{-2}$ (in the degassed water) to $I_{SPTA}$ of 322 W·cm$^{-2}$ (in the NP-PDMS).

The transmitted ultrasonic beam is hypothesized to trigger the mechanochromic and mechanoluminescent transductions via acoustic radiation force (4):

$$F=2\cdot\alpha\cdot I_{SPTA}\cdot c^{-1} \quad [2]$$

where F is the radiation force (force per unit volume, kg·s$^{-2}$·m$^{-2}$) applied along the longitudinal direction, a the absorption coefficient of the material (m$^{-1}$).

Due to the negligible contribution of scattering to attenuation in PDMS samples, the radiation force was estimated using the measured attenuation coefficient, a (Table 2). For instance, with the consideration of the reflected waveform at the surface (18.6%), the calculated volumetric radiation force from the acoustic pressure of 3.2 MPa is approximately 8.46 kg·s$^{-2}$·cm$^{-2}$ for 550 kHz and 10.8 kg·s$^{-2}$·cm$^{-2}$ 1 MHz, respectively. Design of HIFU setup. To evaluate chromogenic responses in PDMS films, a HIFU-based triggering system was designed (FIG. 2A). Note that the acoustic properties of PDMS materials (e.g., speed of sound, attenuation coefficient, etc.) and beam characteristics were measured and summarized. See Kemmerer J P, Oelze M L (2012) Ultrasonic assessment of thermal therapy in rat liver. *Ultrasound Med Biol* 38 (12):2130-2137. The geometry of the sample-holder assembly (FIG. 2A, a3) was considered because force-driven activation is affected by the geometry of the setup. Two ring-shaped polycarbonate plates were employed to circumferentially hold the PDMS samples (FIG. 2A, a3) and the circumferential margin (<5 mm) of the sample was sandwiched between two rings while the center (>45 mm) was freely exposed to degassed water (21±2° C.) in the longitudinal direction (x-direction). There is no substrate in the longitudinal direction that causes the reflection of the pressure field. In this configuration, the size of the beamwidth becomes more than one order of magnitude smaller than that of the sample (with a ratio of 0.05), ensuring the stress development on the focal spot without significant geometric distortions. This enables better understanding of the relationship between HIFU-induced pressure and the mechanophore activation. With this boundary condition, the acoustic pressure applied at the focal spot was estimated. The estimation of the acoustic pressure is only applicable for this boundary condition because for more complicated boundary conditions, e.g., tissue, the boundary-induced intervention should be taken into account for the pressure calibration.

Spatial control of HIFU irradiation was achieved using a computer-controlled micro-positioning system, which allowed the positioning of the sample-holder assembly at the focal distance with better than 2 μm spatial accuracy. The assembly mounted onto the positioning system was precisely placed at the focal distance of the transducer with its face (y-z direction) perpendicular to the beam of the transducer. Thereafter, the focal spot was determined by adjusting the vertical location (z-direction) of the sample assembly. To achieve temporal resolution, the duration and exposure level of continuous wave-HIFU (CW-HIFU) exposure was varied. The results confirmed that by using a short sonication duration of seven seconds and lower exposure levels (acoustic pressure below 3.2 MPa), a transfer of primarily mechanical energy was successfully achieved while minimizing heat-induced bulk material damage that can occur from accumulation of CW-HIFU induced thermal energy into the PDMS films.

In order to control acoustic pressure in the setup, input voltage set in the function generator to the HIFU transducer was first calibrated with the output voltage of the beam at the focal point as recorded by a calibrated hydrophone, and then the conversion of the peak-to-peak amplitude of the output voltage to the acoustic pressure was achieved with the hydrophone sensitivity (FIG. 20A). With this input, the acoustic pressure (or power) of the ultrasound beam at the focus was estimated (FIG. 10B), and thus the corresponding intensity, $I_{SPTA}$ and the radiation force, F (Nightingale et al. (2002) Acoustic radiation force impulse imaging: in vivo demonstration of clinical feasibility. *Ultrasound Med Biol* 28 (2):227-235) were obtained. Based on this, the HIFU-triggering system generates the targeted pressure at the focus during the operation.

Figure 3:
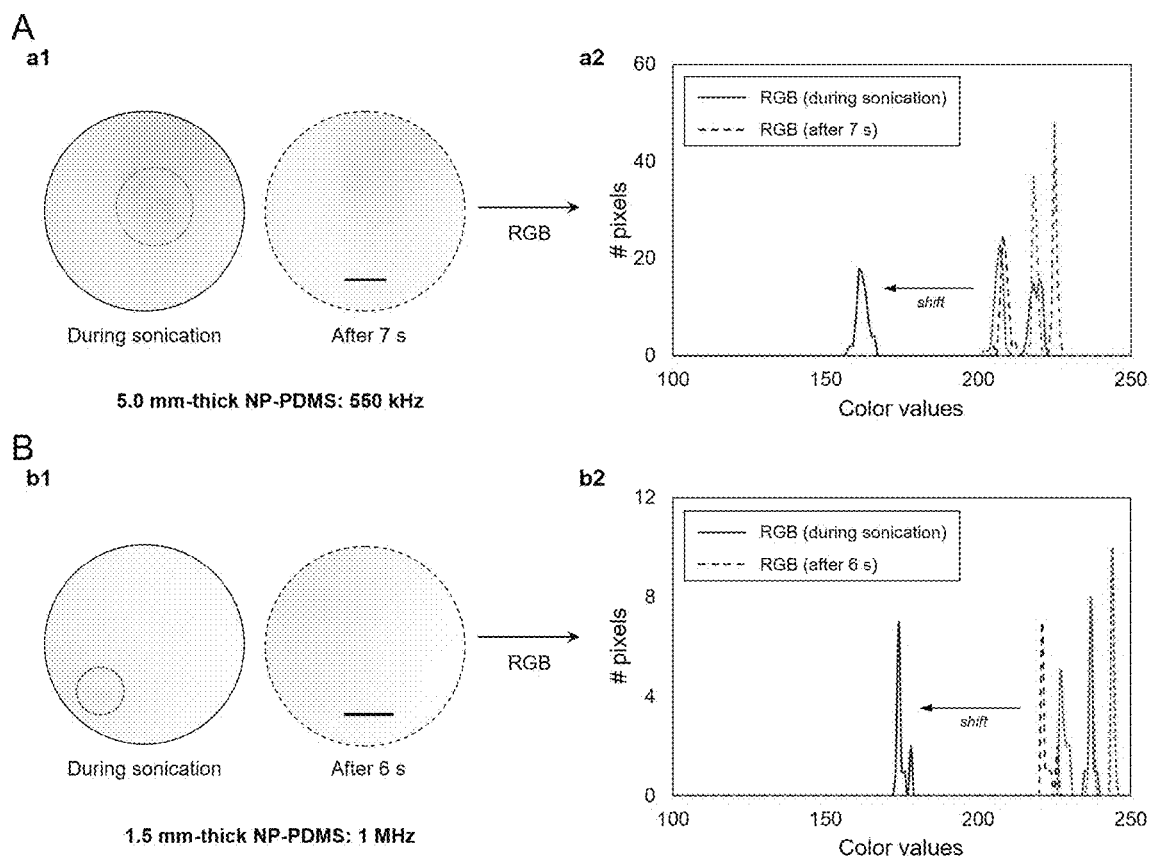
FIG. 3 shows dependency of color change on the excitation frequency. Size of activated area correlates to the wavelength and beamwidth of the transducer. (A) (a1)-(a2) A 550 kHz HIFU transducer results in the colored area having a diameter of 2.7 mm. (B) (b1-b2) A 1 MHz HIFU transducer results in the colored area having a diameter of 1.2 mm. The RGB analysis during sonication provides a color profile that is consistent with NP electrocyclic ring-opening. Scale bar=2.5 mm.
Figure 9:
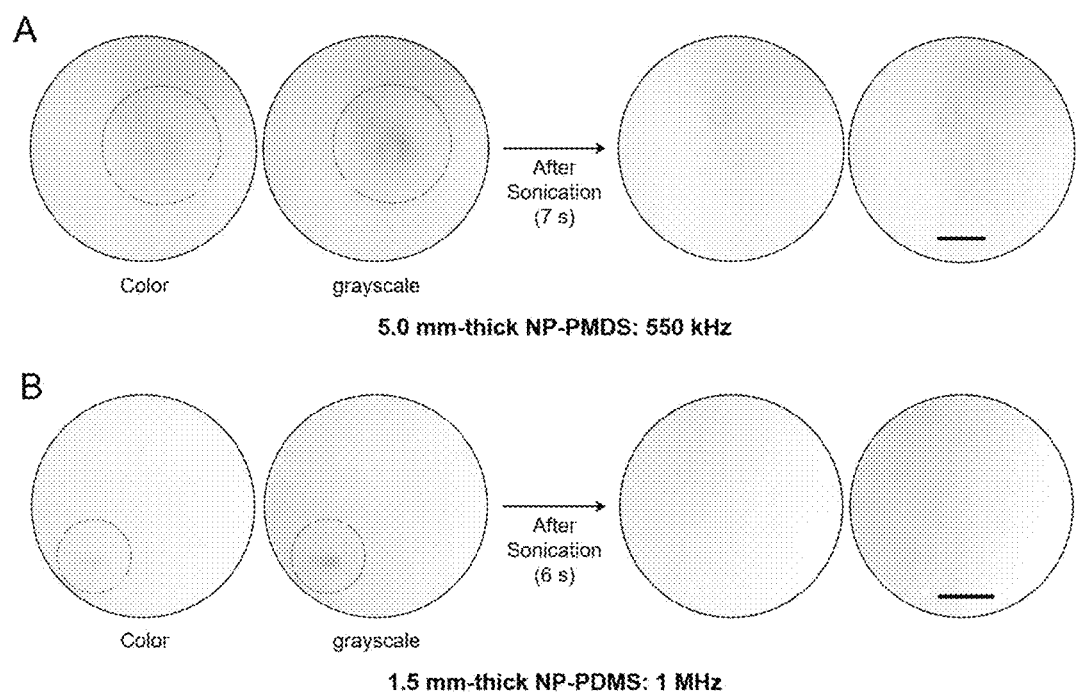
FIG. 9 shows activation of naphthopyran mechanophore in color and grayscale images: (A) 5 mm-thick NP-PDMS film with 550 kHz; and (B) 1.5 mm-thick NP-PDMS film with 1 MHz. Grayscale images explicitly shows the activated area and its dependency on the wavelength of the excitation frequency ($\lambda=c/f$). Scale bar=2.5 mm.

Effect of excitation frequency: 1 MHz vs 550 kHz. The correlation between the mechanochromism of the cross-linked NP and the excitation frequency of the HIFU transducer was examined. A 1 MHz (beamwidth at the focus of 1.2 mm) transducer and a 550 kHz (beamwidth at the focus of 2.2 mm) transducer were used to deliver the same acoustic pressure of 3.2 MPa ($I_{SPTA}$=333 W·cm$^{-2}$) to the target areas of 1.5 mm- and 5.0 mm-thick NP-PDMS films, respectively. Note that the sample thickness was determined based on the depth of field of the transducers. Similar to the results above (FIG. 2C and FIG. 3B), reversible color changes in the regions of the focal spots were observed for both samples—a visible orange coloration appeared during the sonication period, which disappeared within one minute after the end of irradiation (FIG. 3A). However, for the activated area, the diameter of the orange-colored area obtained from irradiation of the 5.0 mm-thick film with a 550 kHz beam was approximately two times larger than that achieved using a HIFU frequency of 1 MHz (FIG. 3 and FIG. 9). This clearly shows that the size of the activated area was determined by the beamwidth of the transducer, supporting the ability of the HIFU setup to modulate the size of mechanophore activation over multiple frequencies. After color dissipation following an initial sonication event, irradiation of the same area resulted in a repeated chromogenic response within the selected pressure level range (2.3 to 3.2 MPa). The RGB analysis also shows a concomitant shift in the blue channel during the HIFU irradiation, while the red and green channels exhibited no significant changes (FIG. 3A a2 and FIG. 3B b2). With a temporal resolution of seven seconds, this consistency demonstrates that the HIFU setup is capable of spatially controlling the activation of NP mechanophore in PDMS.

Example 5

Figure 8:
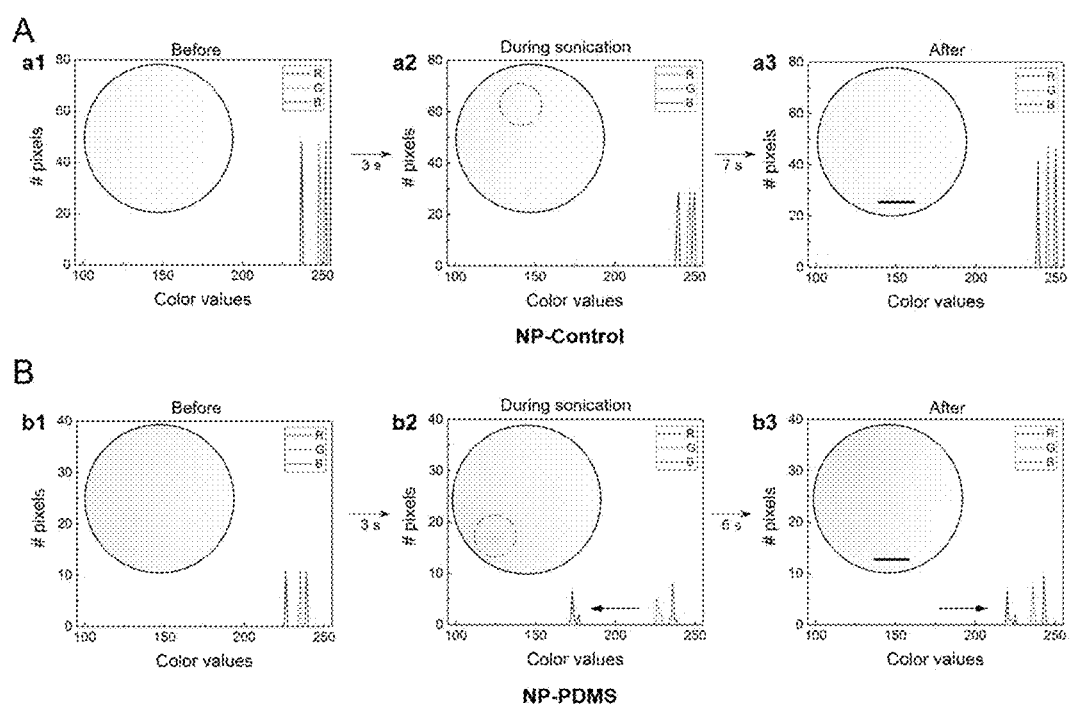
FIG. 8 shows an RGB analysis of mechanochromic response: A (a1-a3) NP-control; and B (b1)-(b3) NP-PDMS. The RGB analysis confirms that the formation of the orange-colored merocyanine species results in significant shift in the blue channel, 226 (before)→74 (during)→221 (after). Scale bar=2.5 mm.

Mechanical activation of NP using HIFU. Having determined the threshold intensity 333 W·cm$^{-2}$) and sonication duration (7 s) to minimize the thermal effects of CW-HIFU irradiation on PDMS, the ability of HIFU to induce a color change in NP-PDMS via mechanical force was evaluated. Using a 1 MHz transducer, a 1.5 mm-thick NP-PDMS film was irradiated with CW-HIFU for seven seconds at 3.2 MPa ($I_{SPTA}$=333 W·cm$^{-2}$). A color change from colorless to orange was visually observed at the focal spot, demonstrating localized mechanophore activation triggered by HIFU irradiation (FIG. 2C, c2 to c4). After sonication, the orange color dissipated under ambient light and temperature within one minute. The color change during HIFU sonication was qualitatively characterized by RGB analysis (FIG. 8).

Figure 5:
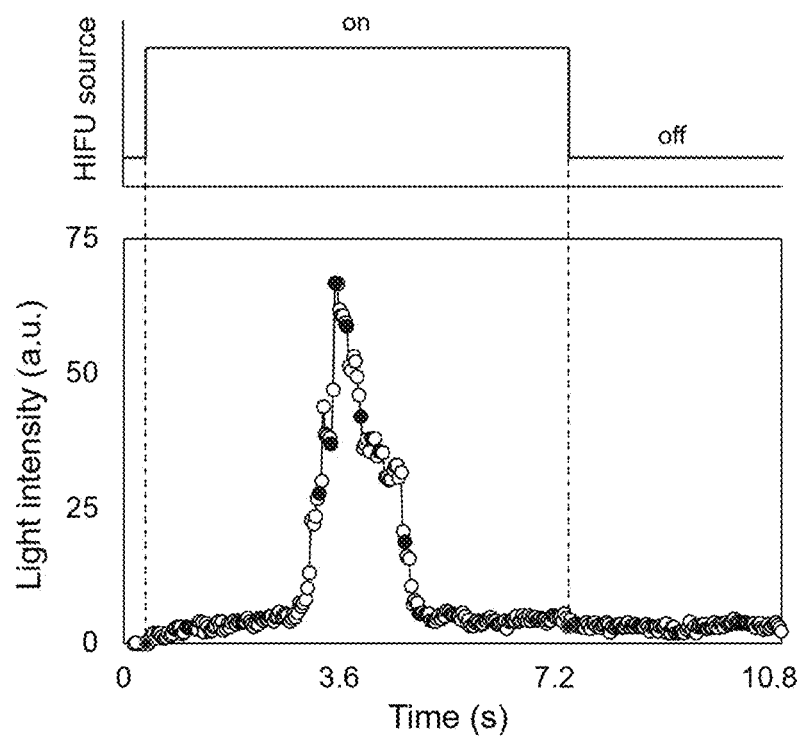
FIG. 5 shows mechanoluminescent behavior of dioxetane-functionalized PDMS: (A) Plot of the generated blue light intensity versus time (a.u.=arbitrary units); and (B) optical images showing the intensity verses on time. The intensity plot is based light generated in the focal spot (approximately 2.25 mm, 1 MHz. Green- and red-colored points in the plot indicate the start and end points of sonication respectively. Scale bar=5.0 mm.
Figure 5:
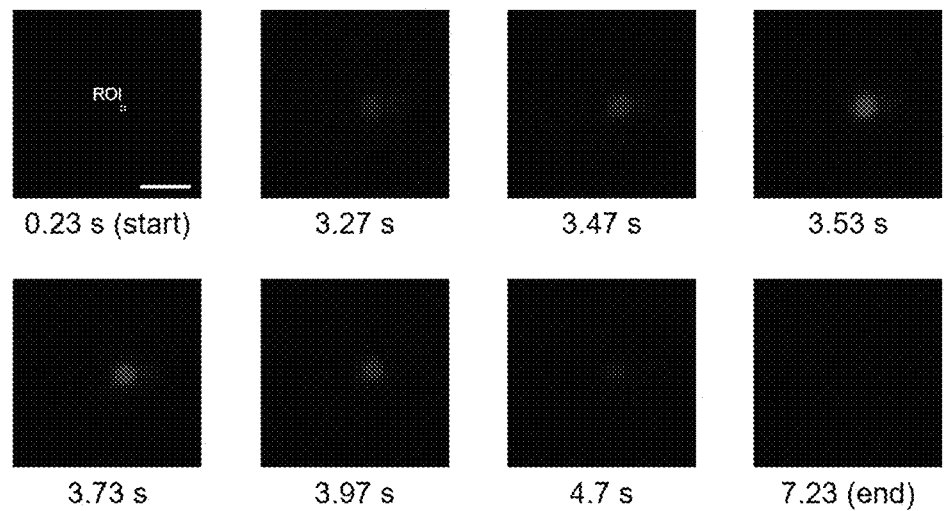

RGB Analysis. Among many methods available for performing image analysis, Image Pro Plus software (Media Cybernetics, Rockville, MD) was used to analyze the mechanophore-induced color change. The video clips were recorded with a waterproof digital camera and were reconstructed with a frame rate of 30 frames per second (fps). Then, the region of interest (ROI) set to be smaller than the colored area was applied through all frames. The ratio of the ROI to the colored area was fixed to less than 0.5 to improve the intensity, and SNR of three RGB peaks. The time-lapse frames shown in FIG. 2 and FIG. 3 were chosen based on the lowest value of the blue channel, and using this value, comparison of each RGB channels (0 to 255) was conducted. In a similar way, the light intensity analysis was also achieved (FIG. 5).

Formation of the orange merocyanine (red=236; green=227; and blue=174) from the colorless NP (red=238; green=234; and blue=226) was characterized by a consistent and significant shift in the blue channel (FIG. 8B and FIG. 3B). Six seconds after HIFU irradiation ceased, the RGB profile returned to values (red=243; green=236; and blue=221) nearly identical to the original sample. These observations are consistent with HIFU-triggered isomerization of NP to highly colored merocyanine, followed by reversion to colorless NP under ambient light after cessation of the HIFU irradiation. Indeed, when the identical focal spot on the NP-PDMS sample was repeatedly sonicated with HIFU, the same colorless-to-orange transition of NP was observed every time followed by color reversion, demonstrating that the mechanochromic behavior was reversible and repeatable and the specific ultrasonic conditions did not cause noticeable chemical damage to NP. Unlike CW-HIFU irradiation, tone burst excitation, even with a duty cycle of 90%, which corresponds to an $I_{SPTA}$ of 300 W·cm$^{-2}$ and a 10% decrease in the radiation force, did not result in visually observable mechanochromism, showing that mechanical force generated with tone burst excitation was not sufficient to activate the NP-PDMS films with a seven second sonication duration.

At the HIFU intensity used ($I_{SPTA}$=333 W·cm$^{-2}$) the contribution of thermal energy to the observed mechanochromism in NP-PDMS is likely negligible. Because a PDMS film of identical dimensions functionalized with the NP-control did not exhibit observable color change when irradiated at this intensity, the primary effect of HIFU in this intensity regime is the transfer of mechanical energy to the PDMS film. The observation of chromogenicity in NP-PDMS is therefore attributed to HIFU-induced triggering of the crosslinked NP mechanophore. Exposing 1.5 mm-thick NP-PDMS films to seven seconds of CW-HIFU irradiation at pressure levels from 2.3 to 3.2 MPa resulted in visibly evident reversible color change (colorless to orange) while the brightness of the orange color corresponded to the applied pressure. Below 2.3 MPa of acoustic pressure ($I_{SPTA}$<172 W·cm$^{-2}$), no distinguishable color change was observed at the focal spot, indicating that at lower intensities, mechanical force applied to the PDMS sample is insufficient to activate the NP mechanophore. At all pressure levels where mechanophore activation was observed, the diameter of the activated colored area was ~1 mm, which is comparable to the estimated beamwidth at the focal spot. This observation suggests that mechanophore activation is localized to the focal spot and the dimension of the colored area is determined by the beamwidth. Taken together, these results indicate that CW-HIFU applied to NP-PDMS at acoustic pressures between 2.3 and 3.2 MPa triggers color change with spatial and temporal resolution corresponding to the focal spot of the HIFU source, thus acting as a trigger for polymer mechanochemistry.

To further rule out thermal activation, a 1.5 mm-thick PDMS film functionalized with the NP-control was exposed to the same CW-HIFU conditions. The NP-control (FIG. 1B) is photo- and thermally activated but does not exhibit color change in response to mechanical deformation. When sonicating NP-control, no visible color change was observed at $I_{SPTA}\leq$333 W·cm$^{-2}$ (3.2 MPa). The absence of color change in the NP-control PDMS suggests that the HIFU sonication does not provide sufficient thermal energy to cause NP isomerization at intensities less than or equal to 333 W·cm$^{-2}$. However, when the film was irradiated with intensities greater than 376 W·cm$^{-2}$ (>3.4 MPa), the focal spot promptly exhibited irreversible material damage and color change due to the thermal threshold being reached (FIG. 2B, b4). Therefore, using this HIFU setup, significant thermal effects can occur at $I_{SPTA}\geq$376 W·cm$^{-2}$, which triggers thermochromism in naphthopyran and also results in irreversible material damage of the PDMS.

Example 6: HIFU Sonication Through Skull: Bio-medical Applications

Figure 4:
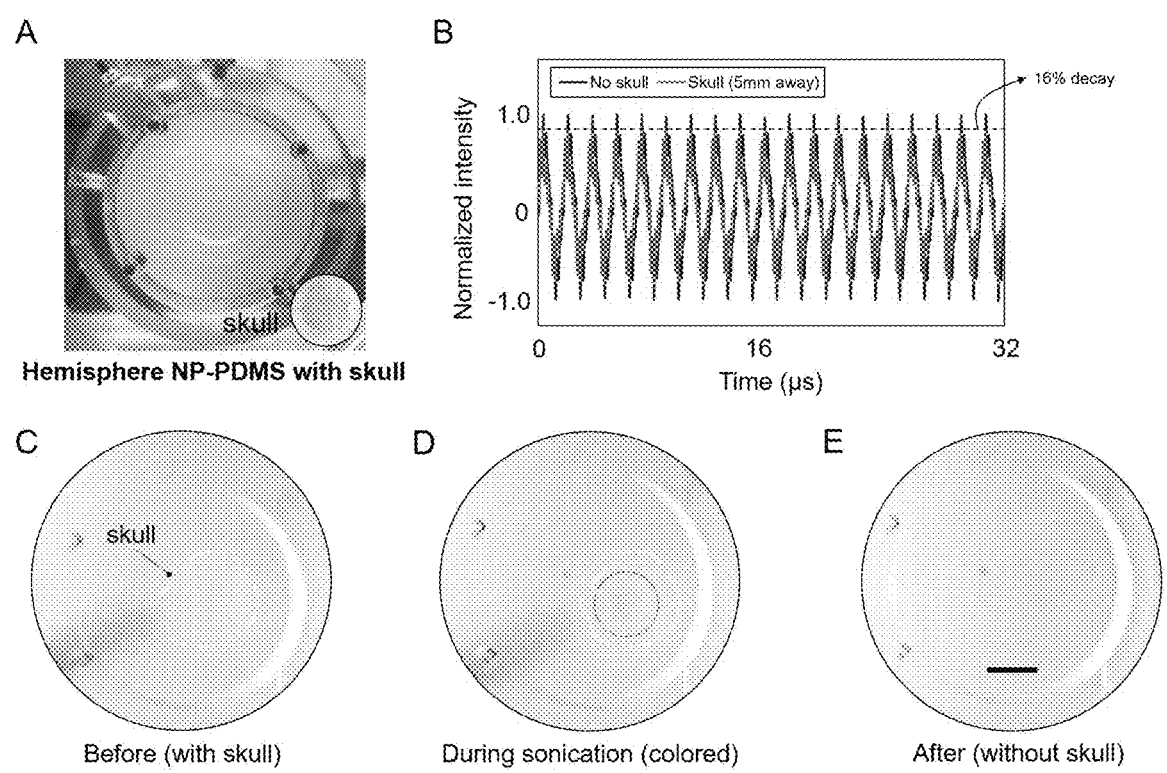
FIG. 4 shows sonication of the hemisphere NP-PDMS through mouse skull tissue (maximum length of 1 cm) with 3.2 MPa: (A) Image of the hemispherical NP-PDMS and prepared skull; (B) attenuated intensity in the time domain signal due to the existence of the skull from hydrophone measurements; (C) skull-NP-PDMS assembly without sonication; (D) colored (orange) area by through-skull sonication (approximate diameter of 1.4 mm); and (E) disappearance of color after sonication. Scale bar=2.5 mm.

HIFU can be used for noninvasive stimulus for drug delivery as it is able to deeply penetrate tissue in comparison to visible and near-infrared (NIR) light. A potential concern for non-invasive in vivo bio-medical applications of HIFU is significant wave distortion (e.g., attenuation) arising from interactions with intervening media such as the skull tissue. To demonstrate the viability of using HIFU as a stimulus to trigger polymer mechanochemistry in a biological context, the activation of polymer mechanochemistry was examined through a sample of mouse skull (approximately 300 to 400 µm thick) that acts as an attenuating and aberrating layer. The skull tissue was attached to the anterior surface of a hemisphere shaped PDMS slab (15 mm at the thickest point) (FIG. 4A). Then, a 550 kHz HIFU transducer was used to propagate the ultrasonic beam behind the surface of the PDMS-skull assembly. First, the energy loss of the ultrasonic beam through the skull was quantified using a hydrophone. As shown in the received time domain signal (FIG. 4B), the presence of the skull tissue reduced the peak intensity amplitude by approximately 16%. Thus, a relatively higher excitation voltage is required for visible color change with intervening tissues, when compared to the sample without tissue layer. The results suggest that the estimated activation threshold pressure and the maximum pressure for this boundary condition are 2.5 and 3.4 MPa ($I_{SPTA}$ of 204 to 376 W·cm$^{-2}$), respectively. Above 3.5 MPa ($I_{SPTA}$=399 W·cm$^{-2}$), the hemisphere PDMS undergoes irreversible thermal ablation rather than exhibiting mechanical irradiation effects. To examine mechanophore activation at different penetration depths, the location of the focal spot from the surface to the back of the assembly was varied in 0.5 mm increments (in the x-direction) and identified that within the hemisphere geometry considered, the acoustic energy achieves the maximum color change in terms of both intensity and diameter of the chromogenic region at approximately 5 mm below the PDMS-skull assembly. Matching the HIFU conditions used with NP-PDMS films, we then sonicated the PDMS-skull assembly using an acoustic pressure of 3.2 MPa ($I_{SPTA}$=333 W·cm$^{-2}$) and irradiation time of seven seconds at this sample depth. During the sonication period, a distinguishable change to orange color was recorded (FIGS. 4C and D), showing that isomerization of NP was achieved by the HIFU irradiation in the target area. Color dissipation was observed within one minute after cessation of HIFU irradiation, demonstrating the reversibility of mechanically-activated NP isomerization (FIG. 4E). HIFU-based triggering of polymer mechanochemistry through a mouse skull demonstrates the potential for in vitro and in vivo applications. Examples include treatment of solid tumors, treatment of abdominal and gynecological disease (e.g. liver, kidney, pancreas, bladder, uterus and vulva diseases), and painful diseases such as musculoskeletal degeneration, bone metastases, and neuropathic pain. With the capability to spatiotemporally control the acoustic pressure, HIFU enables the activation of mechanophore-functionalized biocompatible polymers, facilitating mechanochemical phenomena such as mechanoluminescence in vivo through intervening tissues such as bone.

Example 7: Mechanoluminescence by HIFU

As light is an important stimulus in biomedicine, the ability of HIFU to trigger mechanoluminescence in a PDMS film was tested in order to evaluate the potential of sonication-driven polymer mechanochemistry for such applications. Bis(adamantyl)-1,2-dioxetanes that are functionalized with polymers at both adamantane groups cleave under mechanical force while exhibiting thermal stability up to 150° C. Upon scission of the dioxetane, a weakly luminescent excited-state ketone is formed. In the presence of fluorescent acceptor molecules such as 9,10-diphenylanthracene (DPA), more efficient chemiluminescence is observed (FIG. 1C). Using the data acquired from HIFU experiments on NP-containing PDMS films as references for transducer and pressure settings, 5.0 mm-thick PDMS samples containing 1.5 wt % of covalently incorporated 1,2-dioxetane mechanophore and 0.5 wt % of non-covalently dispersed DPA were sonicated. When the dioxetane-functionalized PDMS was irradiated with a 550 kHz HIFU transducer at the pressure level of 3.2 MPa ($I_{SPTA}$=333 W·cm$^{-2}$) for seven seconds, a distinguishable blue luminescence was observed (wavelength of approximately 420 nm within the focal spot (FIG. 5). Once HIFU transduction stopped, the luminescence diminished immediately. The HIFU activation of mechanoluminescence was recorded with a digital camera and individual frames analyzed to quantify the intensity of luminescence (FIG. 5A). The optical images obtained show the emission, increase, and dilution of the intensity of blue luminescence with increasing time (FIG. 5B). The diameter of the focal spot where the blue luminescence was recorded was almost identical to the beamwidth (ca. 2.2 mm). A control experiment using a PDMS film containing 1.5 wt % 1,2-dioxetane and 0.5 wt % DPA (both non-covalently dispersed in the polymer matrix) did not generate blue light upon HIFU excitation (FIG. 1D). This demonstrates that the 1,2-dioxetane mechanophore can be covalently incorporated into the elastomer in order to elicit photoluminescence upon HIFU irradiation. The same set of ultrasound parameters (frequency and intensity) actuates both the mechanoluminescence of 1,2-dioxetane and the mechanochromism of naphthopyran with similar spatiotemporal precision. In contrast to mechanochromic activation of NP that occurs through an electrocyclic isomerization that is reversible via the absorption of energy from the visible light, mechanical activation of the 1,2-dioxetane mechanophore results in irreversible cycloelimination. When using HIFU to irradiate the same focal spot on a 1,2-dioxetane—functionalized PDMS film, only a few repetitions of light emission were possible, which is consistent with the irreversible consumption of mechanophores upon mechanical cleavage of the 1,2-dioxetane ring. Overall, HIFU activates mechanoluminesence in a PDMS polymer matrix, allowing control of light generation through a remote, non-invasive stimulus. By exploiting current advances in mechanophore-based chemoluminescence, the coupling of polymer mechanochemistry with HIFU techniques will facilitate the development of functional optogenetic tools.

These examples demonstrate for the first time that HIFU is an efficient stimulus for noninvasive activation of polymer mechanochemistry in elastomeric PDMS networks. The advantage of the proposed method over existing triggering methods is the capability to achieve spatiotemporal control of mechanophore activation. In particular, the HIFU-based triggering system demonstrated here is a remote energy source capable of localizing the region of activation and triggering polymer mechanochemistry noninvasively. These advances enable mechanoactivation of at least two different mechanophore systems. Both the isomerization of naphthopyran and the cycloelimination of 1,2-dioxetane were achieved using mechanical energy delivered from HIFU irradiation, leading to color change or blue light emission within the focal spot on functionalized PDMS films. Given the broad library of available productive mechanophores, HIFU-based triggering systems will open a new route for exploiting polymer mechanochemistry for biomedical applications, e.g., the use of mechanoluminescent polymer systems to generate a localized photon flux noninvasively.

Example 8. Methods of Preparation of Dioxetane

Dioxetane does not require external light for luminescence to occur. That is, dioxetane is a mechanophore that luminesces under force without external light energy. A method of preparation of dioxetane based on *J. Am. Chem. Soc.*, 2015, 137 (20), pp 6577-6586 (DOI: 10.1021/jacs.5b01555) is shown below.

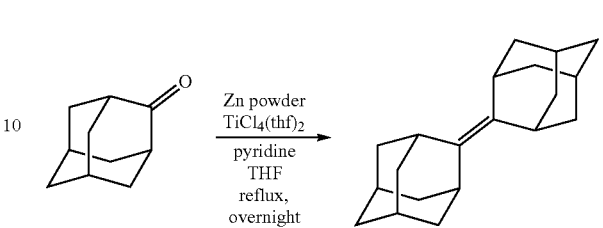

Reagents:
  2-adamantanone (Acros Organics)
  TiCl$_4$(thf)$_2$ (Sigma-Aldrich)—a free-flowing yellow powder. Store in desiccator.
  Zinc powder (Aldrich)—should be a pale silver color. If dark silver, then activate by stirring in 1M HCl overnight, then filter and wash with THF. Dry on vacuum line before use. Activated Zn will store for a couple of months in a sealed container.
  Pyridine (anhydrous, SureSeal from Aldrich)
  THF (dry, from solvent system)
  Procedure: A large Schlenk flask was flame dried with stir bar, then charged with TiCl$_4$(thf)$_2$ (10.22 g, 30.6 mmol, 2.3 equiv) under N$_2$. 40 mL of THF was added via syringe, and the mixture cooled to 0° C. Zinc powder (4.06 g, 61.2 mmol, 4.6 equiv) was added portion-wise, then the cooling bath removed and the reaction heated to reflux—a dark greenish-brown solution is formed. After 1 hour reflux, the reaction was cooled to 0° C. again, and pyridine (1.25 mL, 1.23 g, 15.5 mmol, 1.15 equiv) was added via syringe. A solution of 2-adamantanone (2.0 g, 13.3 mmol) dissolved in 40 mL of THF was then added via cannula to the reaction. The cooling bath was removed, and the reaction refluxed overnight. The reaction was cooled to room temperature, then quenched by adding 100 mL of K$_2$CO$_3$(aq) solution (10 wt %)—add carefully, sometimes quench evolves gas. The mixture was stirred for 5 min, and then vacuum filtered through a Celite plug to remove a silvery paste and zinc metal. The filtrant was poured into a separatory funnel, diluted with Et$_2$O, and washed with H$_2$O followed by brine. The organic layer (a pale yellow or colorless solution) was dried on MgSO$_4$, filtered, and evaporated to dryness giving an off-white solid as the crude product. The crude product was purified by manual column chromatography by loading the product as a solution in CHCl$_3$, and eluting with 100% hexanes. The product is only visible by I$_2$ staining, R$_f$~0.7 in 100% hexanes. Obtained 1.25 g (4.7 mmol, 70% yield) as colorless crystals.

On 2.0 g scale, 70% yield is typical. On 1.0 g scale, 90-98% yield is achievable. 1H NMR (CDCl$_3$, 500 MHz) δ (ppm): 2.90 (4H, br s); 1.92 (4H, br s); 1.86-1.79 (12H, m); 1.70-1.64 (8H, m) 13C NMR (CDCl$_3$, 125 MHz) δ (ppm): 133.26, 39.75, 37.48, 32.02, 28.69.

Another Dioxetane was prepared based on Russian Journal of Organic Chemistry, 2015, Vol. 51, No. 2, pp. 184-187 (DOI: 10.1134/S1070428015020074) as follows:

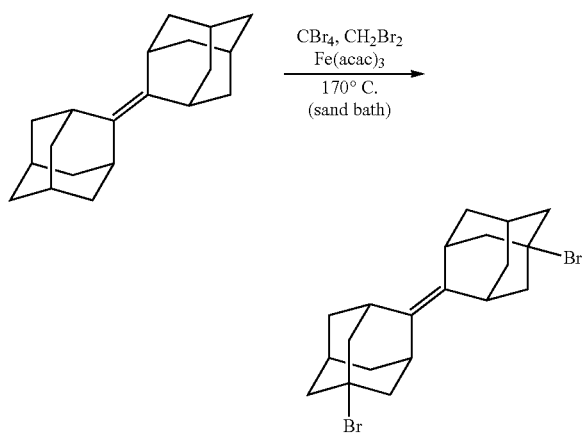

Reagents:
Adamantane dimer (805.3 mg, 3 mmol)
Dibromomethane (Aldrich) (15.65 g, 6.32 mL, 90 mmol)
Fe(acac)$_3$ (Aldrich) (63.6 mg, 0.18 mmol)
CBr$_4$ (Aldrich) (1.99 g, 6 mmol)

Procedure: All reagents were charged to a flame-dried 25 mL Schlenk flask, then flushed with N$_2$, and the flask sealed with a new septum and electrical tape (reaction will build pressure from heating). The sealed flask was heated to 170° C. in a sand bath under a foil tent to protect from light and for insulation. After heating overnight, the reaction (a red-brown solution) was cooled to room temperature, evaporated to dryness, then re-dissolved with CH$_2$Cl$_2$ and eluted through a basic alumina plug, then evaporated to dryness and purified by manual column chromatography (100% Hexanes → 1:1 Hexanes/Et$_2$O → 100% Et$_2$O).

Using this method, some mono-brominated product and some starting material is usually recovered. The desired product elutes as a streaky brown fraction, and only starts to elute when the eluent contains Et$_2$O. The mono-brominated product and starting material will elute from 100% hexanes (1$^{st}$ fraction=starting material; 2$^{nd}$ fraction=mono-brominated product; 3$^{rd}$ fraction=di-brominated product). The dibrominated product will solidify on the test tubes as it elutes. All brown-colored fractions were collected and used for the following reaction.

Alternative synthesis Following literature prep. from E. W. Meijer's thesis ("Chemiluminescence in action: syntheses, properties, and applications of 1,2-dioxetanes" 1982, University of Groningen).

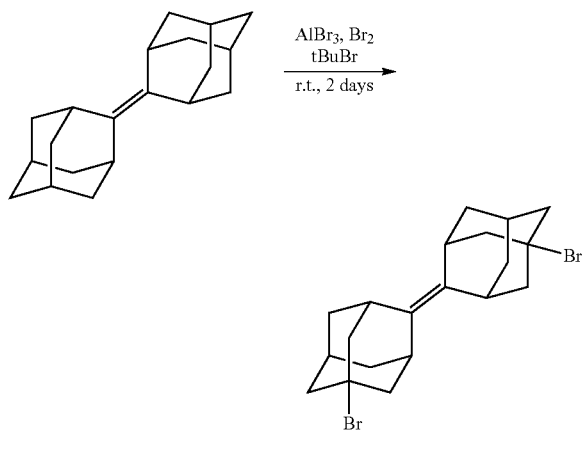

Reagents:
Adamantane dimer (805.3 mg, 3 mmol)
AlBr$_3$ (Strem) (3.87 g, 14.5 mmol, 4.8 equiv)—store in container with Drierite; a fuming solid.
Bromine (2.89 g, 0.93 mL, 18.1 mmol, 6 equiv)
Tert-butyl bromide (0.387 mL, 472 mg, 3.45 mmol, 1.15 equiv)

Procedure: In a tared Schlenk flask in the fume hood, weigh out AlBr$_3$ (add AlBr$_3$ to flask seal with septum, then weigh by difference; can use more than 4.8 equiv). Add adamantane dimer, tBuBr, then bromine—the reaction mix will fume copiously. Seal quickly with a fresh septum, then seal with electrical tape. The flask will fill with bright orange fumes. Swirl the flask to mix all components, and then set in a beaker in the fume hood for 2 days.

Open flask carefully—fumes will be released. Use CH$_2$Cl$_2$ to transfer flask contents into a separatory funnel containing ice-cold water. Extract the aqueous layer with CH$_2$Cl$_2$ 3×, then combine organic layers and wash with Na$_2$S$_2$O$_3$ (aq., saturated) until bromine is quenched (the aqueous layer should no longer be turbid). Add Na$_2$S$_2$O$_3$ carefully as reaction with bromine can be violently exothermic. Dry organic layer on MgSO$_4$, then filter and evaporate. The product will be a brown-black oil/solid. Purify by eluting through basic alumina with CH$_2$Cl$_2$. At this point, the product is clean enough to use for the following reaction, but can be further purified by stirring with activated charcoal overnight to decolor (will become a yellow solid), or column chromatography using 1:1 hexanes: Et$_2$O. This procedure does not yield mono-brominated product or recovered starting material. After purification gives ~80-90% yield (obtained 85% yield on 1.0 g scale, see VL03P007). Without purification, aluminum salts remain and mass balance is>>quantitative yield.

Monobrominated Product:
1H NMR (500 MHz, CDCl$_3$) δ (ppm): 3.07 (2H, bs), 2.86 (2H, bs), 2.45-2.40 (3H, m), 2.37-2.22 (4H, m), 2.16 (1H, bs), 1.95-1.90 (2H, m), 1.88-1.79 (7H, m), 1.70-1.61 (6H, m)

Di-brominated Product:
1H NMR (500 MHz, CDCl$_3$) δ (ppm): 3.04 (4H, bs), 2.47-2.41 (8H, m), 2.32-2.25 (4H, m), 2.16 (2H, bs), 1.88-1.80 (4H, m), 1.69-1.61 (4H, m).

The following compound was made based on *Nature Chemistry* volume 4, pages 559-562 (2012) (DOI: 10.1038/nchem.1358).

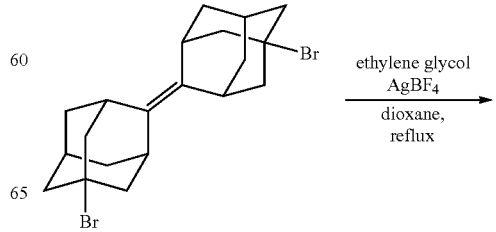

-continued

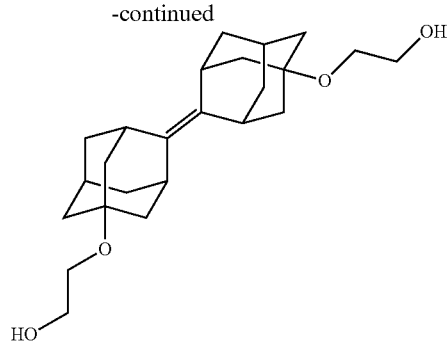

-continued

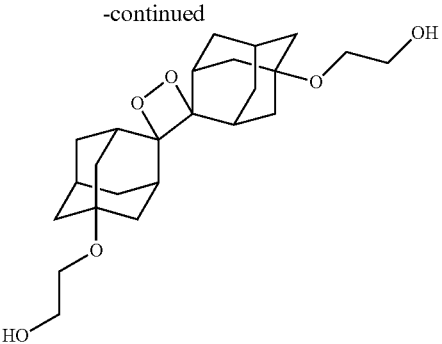

Reagents:
  Bromo-adamantane dimer (1.37 g crude, ~3.2 mmol)
  Ethylene glycol (anhydrous, SureSeal from Aldrich) (50 mL, 55.5 g, 0.9 mol, 280 equiv)
  $AgBF_4$ (Aldrich) (2.4 g, 12.3 mmol, 3.8 equiv)
  1,4-dioxane (anhydrous, Acros Seal with molecular sieves) (15 mL)

Procedure: A 200 mL Schlenk flask was flame dried with stir bar, then charged with bromo-adamantane dimer under $N_2$ atmosphere. Dioxane was added via syringe followed by ethylene glycol. $AgBF_4$ was weighed out quickly and added in 1 portion. The reaction flask was heated to 100° C. under a foil tent to protect from light for 6 hours.

After cooling to room temperature, the reaction was diluted with $Et_2O$ and then poured into a separatory funnel with $H_2O$. The aqueous layer was extracted with $Et_2O$, 3×—a grey-brown precipitate forms (silver salts). The organic layer was washed with brine, and then dried on $MgSO_4$ to give the crude product as a thick brown oil. The crude product was loaded onto a 25 G $SiO_2$ column and purified on the Biotage eluting with 0%→10% MeOH/$CH_2Cl_2$ ramp over 10 CV, then 10% MeOH/$CH_2Cl_2$ for 10 CV. The product absorbs at <220 nm and is detected by the Biotage, but collect all fractions and TLC (MeOH:$CH_2Cl_2$ 1:9) with $I_2$ or $KMnO_4$ stain to visualize. Sometimes 2-3 regioisomers can appear as separate spots on TLC but usually a single large spot is seen. If the product is very brown, stirring with activated charcoal will decolor. 791 mg of a waxy light yellow solid (2.04 mmol, 64%) was obtained.

1H NMR (400 MHz, $CDCl_3$) δ (ppm): 3.7-3.65 (4H, m or complex quartet), 3.51 (4H, t, J=5.5 Hz), 3.10 (4H, bs), 2.24-2.14 (4H, m), 1.85-1.78 (8H, m), 1.74-1.65 (8H, m), 1.61-1.54 (4H, m).

Following procedures from *Nature Chemistry* volume 4, pages 559-562 (2012) (DOI: 10.1038/nchem.1358) and Jess Clough, "Mechanoluminescent probes in polymers," Thesis, T U Eindhoven, 2016, the following compound was synthesized.

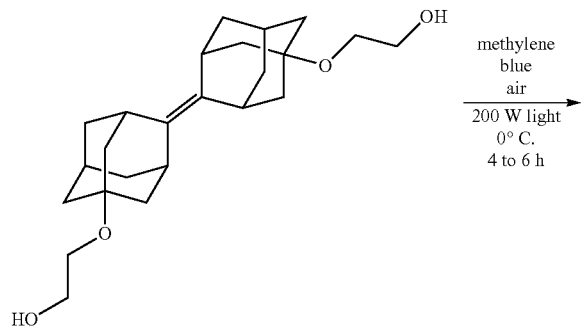

methylene
blue
air
⎯⎯⎯⎯→
200 W light
0° C.
4 to 6 h

Reagents:
  glycol-adamantane dimer (155 mg, 0.4 mmol)
  $CH_2Cl_2$ (from solvent system) (20 mL)
  Methylene blue hydrate (Aldrich) (5.4 mg)

Procedure: A septum-capped vial (40 mL) was charged with a new Teflon-coated stir bar, glycol-adamantane dimer and methylene blue. A new stir bar or a stir bar that has not been used in metal-containing reactions was used as metal salts catalyze the decomposition of dioxetanes (see Hummelen, J. C., Luider, T. M., Oudman, D., & Wynberg, H. (1991). "1,2-Dioxetanes: Luminescent and Nonluminescent Decomposition, Chemistry, and Potential Applications"). The exact quantity of methylene blue is not important, but keep concentration at ~2 mg/10 mL or less to avoid aggregation in solution which can decrease $^1O_2$ yield and also complicate its removal with activated charcoal after the reaction.

$CH_2Cl_2$ was added to dissolve, and then the solution bubbled with air from a balloon to oxygenate. In this reaction, methylene blue is the photosensitizer, which is excited by visible light (abs. bands at ~400 nm and 630 nm) and then collision with $O_2$ in solution produces excited singlet oxygen ($^1O_2$), which undergoes 2+2 cyclization with the adamantane dimer. A Teflon tube was used to oxygenate, in order to avoid touching the solution with a metal needle.

The reaction was placed into a dry ice/water bath in a 600 mL beaker. The vial was placed nearest to the side of the beaker where the light will be set up. Dry ice was added to the water bath for more durable cooling. The reaction was stirred vigorously and the 200W light source (GE Crystal Clear incandescent bulb) was set up ~6 inches from the reaction. The reaction was irradiated for 4-6 hours, and checked by 1H NMR in $CDCl_3$ every ~2 h to see conversion. Characteristic peaks: 3.10 ppm=starting material; 2.83 ppm=desired product; 2.63 ppm=adamantanone from dioxetane decomposition. After complete conversion, the light source was removed, ~500 mg of activated charcoal was added, and the reaction was stirred overnight at room temperature. The reaction was filtered through a Celite plug and evaporated to dryness. The product can be used immediately for the next reaction.

Puncture the septum with thick needle (16G) and thread Teflon tubing over needle;
  Use a 2$^{nd}$ needle as an outlet for bubbling;
  The tubing/needle joint should be under the septum cap in order to avoid solution trying to escape through the joint;
  Use a piece of foil as a mirror to reflect light back onto the solution.

35

Functionalization for Hydrogel Incorporation

Synthesis of 5,5'/7'-bismethacrylate-5,5'/7'-dihydroxyethylenoxy-adamantylideneadamantane 1,2-dioxetane

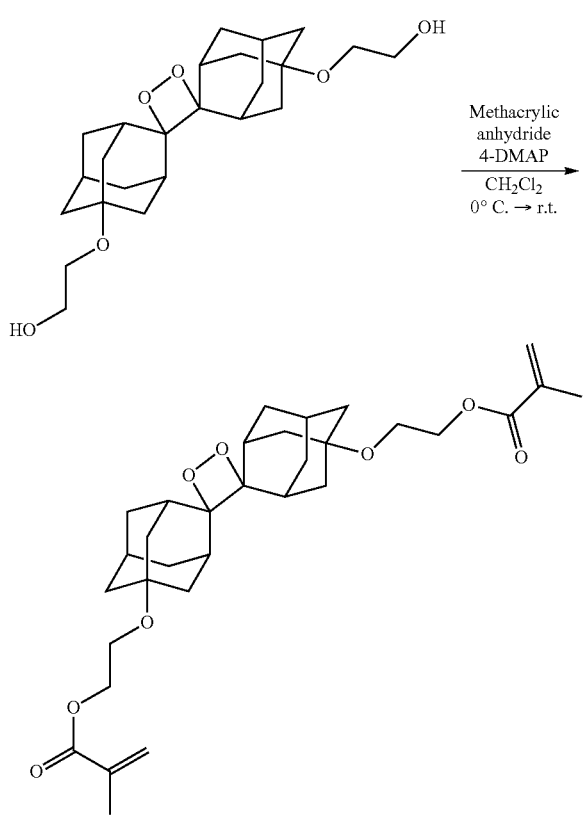

Reagents:
  adamantyl dioxetane diol (carried through from previous reaction, assumed 0.4 mmol)
  methacrylic anhydride (Aldrich) (160 mg, 0.155 mL, 1.04 mmol, 2.6 equiv)
  4-DMAP (Aldrich) (122 mg, 1 mmol, 2.5 equiv)
  $CH_2Cl_2$ (dry, solvent system) (12 mL)

Procedure: Adamantyl dioxetane diol was charged to a 50 mL rbf, then 4-DMAP and a metal-free stir bar added. The flask was evacuated and filled with $N_2$ 3×. $CH_2Cl_2$ was added via syringe, then the reaction cooled to 0° C. Methacrylic anhydride was added slowly via syringe. The cooling bath was removed after 15 min, and then the reaction stirred to room temperature over 2 h.

The reaction was evaporated to dryness and loaded onto a 12G $SiO_2$ cartridge using $CH_2Cl_2$ and purified on the Biotage using a 0%→10% MeOH/$CH_2Cl_2$ gradient (ramp over 15 CV). The desired product shows a UV absorbance peak at ~220 nm (from acryloyl group); DMAP and DMAP-$H^+$ elute afterward and absorb at 220 & 280 nm. The product cross-links at ambient temperature. The product was stored in the presence of an inhibitor (i.e., BHT or hydroquinone).

36

Functionalization for PDMS Incorporation 5,5'/7'-bispent-4-enoate-5,5'/7'-dihydroxyethylenoxy-adamantylideneadamantane 1,2-dioxetane

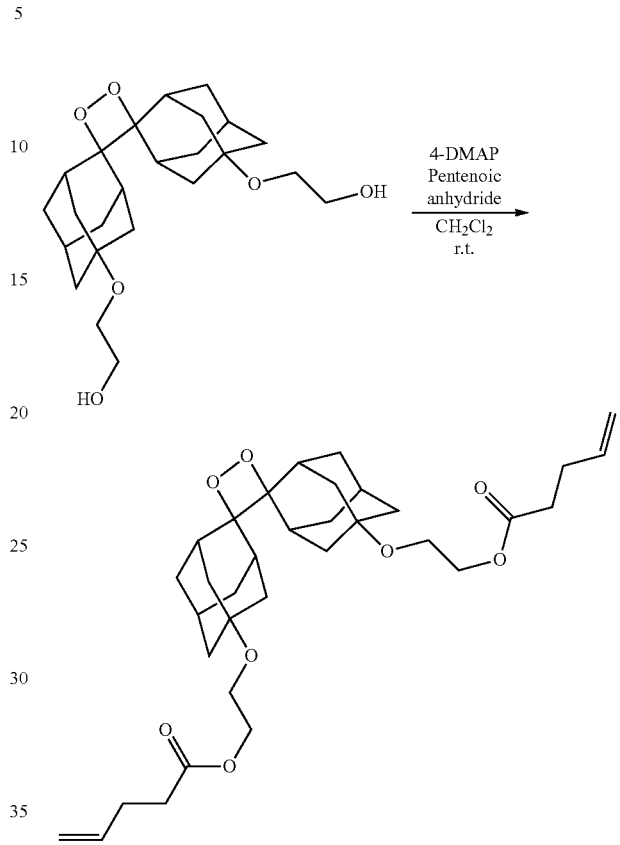

Reagents:
  adamantyl dioxetane diol (100 mg, 0.238 mmol, 1 equiv)
  Pentenoic anhydride (Aldrich) (108.3 mg, 0.595 mmol, 2.5 equiv)
  4-DMAP (Aldrich) (72.7 mg, 0.595 mmol, 2.5 equiv)
  $CH_2Cl_2$ (dry, solvent system) (10 mL)

Procedure: Adamantyl dioxetane diol was charged to a 50 mL rbf, then 4-DMAP and a metal-free stir bar added. The flask was evacuated and filled with $N_2$ 3×. $CH_2Cl_2$ was added. Pentenoic anhydride was added by syringe and the reaction was allowed to stir at room temperature for 18 hours.

0.5 mL methanol was added to the reaction and allowed to stir for 10 minutes. The reaction was evaporated to dryness and loaded onto a 25G $SiO_2$ cartridge using $CH_2Cl_2$ and purified on the Biotage using a 0%→10% MeOH/$CH_2Cl_2$ gradient (ramp over 15 CV). The desired product is a slightly yellow oil.

We claim:

1. A composition comprising a chromogenic or luminescent mechanophore covalently linked to a gel matrix, wherein the chromogenic or luminescent mechanophore is present in the gel matrix at about 1.0 wt % to about 5 wt %, wherein the chromogenic or luminescent mechanophore is naphthopyran, dioxetane, spiropyran, maleimide, or tetraarylsuccinonitrile tetraol, and wherein one or more types of genetically modified cells that express one or more recombinant light sensitive proteins are present within the gel matrix.

2. A composition comprising a chromogenic or luminescent mechanophore covalently linked to a gel matrix, wherein the chromogenic or luminescent mechanophore is present in the gel matrix at about 1.0 wt % to about 5 wt %, wherein the chromogenic or luminescent mechanophore is naphthopyran, dioxetane, spiropyran, maleimide, or tetraarylsuccinonitrile tetraol, and wherein one or more types of genetically modified cells are present within the gel matrix, wherein the composition further comprises an energy acceptor.

3. The composition of claim 2 wherein the energy acceptor is perylene, anthracene, or psoralen.

4. The composition of claim 2, wherein the energy acceptor is present in the gel matrix at about 0.1 wt % to about 10 wt %.

5. The composition of claim 1, wherein the matrix is in contact with cells, cell culture, or tissue.

6. A composition comprising anthracene covalently linked to a gel or elastomer matrix, wherein the anthracene is present in the gel or elastomer matrix at about 1.0 wt % to about 5 wt %, wherein one or more types of genetically modified cells that express one or more recombinant light sensitive proteins are present within the gel or elastomer matrix.

7. The composition of claim 6, wherein the gel or elastomer matrix comprises polydimethylsiloxane (PDMS) or polyethylene glycol (PEG).

8. The composition of claim 6, wherein the composition further comprises an energy acceptor.

9. The composition of claim 8, wherein the energy acceptor is perylene, anthracene, or psoralen.

10. The composition of claim 8, wherein the energy acceptor is present in the gel or elastomer matrix at about 0.1 wt % to about 10 wt %.

11. The composition of claim 6, wherein the gel or elastomer matrix is in contact with cells, cell culture, or tissue.

12. A composition comprising a chromogenic or luminescent mechanophore covalently linked to a gel or elastomer matrix, wherein the chromogenic or luminescent mechanophore is present in the gel or elastomer matrix at about 1.0 wt % to about 5 wt %, wherein one or more types of genetically modified cells are present within the gel or elastomer matrix, and wherein the composition further comprises an energy acceptor that is different from the chromogenic or luminescent mechanophore.

13. The composition of claim 12, wherein the chromogenic or luminescent mechanophore is naphthopyran, dioxetane, spiropyran, maleimide, anthracene, or tetraarylsuccinonitrile tetraol.

14. The composition of claim 12, wherein the energy acceptor is perylene, anthracene, or psoralen.

15. The composition of claim 12, wherein the energy acceptor is present in the gel or elastomer matrix at about 0.1 wt % to about 10 wt %.

16. The composition of claim 12, wherein the one or more types of genetically modified cells express one or more recombinant light sensitive proteins.

17. The composition of claim 12, wherein the gel or elastomer matrix is in contact with cells, cell culture, or tissue.

* * * * *